United States Patent
Heinz et al.

(10) Patent No.: US 7,183,458 B1
(45) Date of Patent: Feb. 27, 2007

(54) Δ6 ACETYLENASE AND Δ6-DESATURASE FROM CERATODON PURPUREUS

(75) Inventors: Ernst Heinz, Hamburg (DE); Sten Stymne, Svalöv (SE); Michael Lee, Malmoe (SE); Thomas Girke, Poway, CA (US); Petra Sperling, Hamburg (DE); Ulrich Zaehringer, Borstel (DE)

(73) Assignee: BASF Plant Science GmbH, Ludwigshafen (DE)

( * ) Notice: Subject to any disclaimer, the term of this patent is extended or adjusted under 35 U.S.C. 154(b) by 233 days.

(21) Appl. No.: 09/980,468

(22) PCT Filed: Jun. 7, 2000

(86) PCT No.: PCT/EP00/05274

§ 371 (c)(1),
(2), (4) Date: Dec. 3, 2001

(87) PCT Pub. No.: WO00/75341

PCT Pub. Date: Dec. 14, 2000

(30) Foreign Application Priority Data

Jun. 7, 1999 (DE) ............................. 199 25 718
Dec. 22, 1999 (DE) ............................. 199 62 409

(51) Int. Cl.
*A01H 5/00* (2006.01)
*C12N 15/82* (2006.01)

(52) U.S. Cl. .................. 800/298; 800/281; 536/23.2; 435/252.3; 435/320.1

(58) Field of Classification Search ............ 536/23.2, 536/23.6; 800/281, 298; 435/69.1, 320.1, 435/468, 471
See application file for complete search history.

(56) References Cited

U.S. PATENT DOCUMENTS

| | | | |
|---|---|---|---|
| 4,987,071 A | 1/1991 | Cech et al. |
| 5,116,742 A | 5/1992 | Cech et al. |
| 5,504,200 A | 4/1996 | Hall et al. |
| 5,608,152 A | 3/1997 | Kridl et al. |
| 5,614,393 A | 3/1997 | Thomas et al. |

FOREIGN PATENT DOCUMENTS

| | | |
|---|---|---|
| EP | 249 676 | 12/1987 |
| EP | 335 528 | 10/1989 |
| EP | 388 186 | 9/1990 |
| EP | 550 162 | 7/1993 |
| EP | 794 250 | 9/1997 |
| WO | 91/13972 | 9/1991 |
| WO | 91/13980 | 9/1991 |
| WO | 93/06712 | 4/1993 |
| WO | 93/11245 | 6/1993 |
| WO | 93/21334 | 10/1993 |
| WO | 94/11516 | 5/1994 |
| WO | 94/18337 | 8/1994 |
| WO | 95/15389 | 6/1995 |
| WO | 95/18222 | 7/1995 |
| WO | 95/19943 | 7/1995 |
| WO | 95/23230 | 8/1995 |
| WO | 96/13591 | 5/1996 |
| WO | 96/21022 | 7/1996 |
| WO | 97/21340 | 6/1997 |
| WO | 97/30582 | 8/1997 |
| WO | 97/37033 | 10/1997 |
| WO | 98/45461 | 10/1998 |
| WO | 98/46763 | 10/1998 |
| WO | 98/46764 | 10/1998 |
| WO | 99/16890 | 4/1999 |
| WO | 99/27111 | 6/1999 |

OTHER PUBLICATIONS

Broun et al, Science 282: 131-133, Nov. 13, 1998.*
Van de Loo et al, Proc Natl. Acad Sci, USA, 92: 6743-6747, Jul. 1995.*
Doerks et al, TIG 14(6): 248-250, Jun. 1998.*
Smith et al, Nature Biotechnology 15: 1222-1223, Nov. 1997.*
Brenner, S. E., TIG 15(4): 132-133, Apr. 1999.*
Bork et al, TIG 12(10): 425-427, Oct. 1996.*
De Luca, V, AgBiotech News and Information 5(6): 225N-229N, 1993.*
The Plant Jrl., 1992, 2, 233-239, Baeumlein et al.
EMBO Jrl., vol. 3, No. 4, 835-846, 1984, Gielen et al.
Critical Reviews in Plant Sciences, 15(4):285-423 (1996, Kermode.
Plant Molecular Bio., 20: 1195-1197, 1992, Becker et al.
Nucleic Acids Res., vol. 12, No. 22, 1984, Bevan, 8711-8721.
Nature vol. 329, Oct. 29, 1987, Seed, 840-842.
EMBO Jrl., vol. 6, 1987, No. 1, 187-193, Kaufmann et al.
I. Engineering Transgenic Plants, 4. Techniques for Gene Transfer, 128-146.
Nature vol. 334, Aug. 18, 1988, Haseloff et al., 585-591.
Science, vol. 261, Sep. 10, 1993, Bartel et al., 1411-1418.

(Continued)

*Primary Examiner*—Elizabeth F. McElwain
(74) *Attorney, Agent, or Firm*—Novak Druce & Quigg LLP

(57) ABSTRACT

The present invention relates to a process for preparing unsaturated fatty acids and to a process for preparing triglycerides with an increased content of unsaturated fatty acids. The invention further relates to the use of DNA sequences coding for Δ6-acetylenase/Δ6-desaturases or Δ6-desaturases for producing a transgenic organism, preferably a transgenic plant or a transgenic microorganism with increased content of fatty acids, oils or lipids with Δ6 triple bonds and/or Δ6 double bonds.

The invention additionally relates to an isolated nucleic acid sequence; to an expression cassette comprising a nucleic acid sequence, a vector and organisms comprising at least one nucleic acid sequence or expression cassette. The invention additionally relates to unsaturated fatty acids and triglycerides with an increased content of unsaturated fatty acids and the use thereof.

14 Claims, 1 Drawing Sheet

OTHER PUBLICATIONS

Nucleic Acids Res., vol. 20, Supplement 2111-2118, Wada et al.
Applications of DNA shuffling to pharmaceuticals and vaccines, Patten et al., 724-733.
Jrl.Molecular Bio., vol. 272, No. 1, Sep. 12, 1997, Moore et al. 336-347.
Cell, vol. 21, No. 1, Aug. 1980,Guilley et al, 285-294.
Plant Molecular Bio., Vo. 22, 1993,Ward et al., 361-366.
Nucleic Acids Res., vol. 15, No. 21, 1987, Gallie et al.8693-8711.
Yeast, vol. 8, No. 1, Jan. 1992, Romanos et al., 423-488.
Appl. of Recombinant DNA Tech., Skatrud, 369-424.
Methods in Plant Molecular Bio. and Biotech., Procedures for Introducing Foreign DNA into Plants, 71-119.
Gene, 69 (1988) 301-315, Amann et al.
Gene, 67 (1988)31-40, Smith et al.
Methods in Enzymology, vol. 185, Gene Expresion Technology, Expression in *E. coli*, Studier, 60-89.
The Embo Jrl., vol. 6,No. 1, 1987,Baldari et al., 229-234.
Cell, vol. 30, No. 2, Sep. 1992, Kurjan et al., 933-943.
Gene,54 (1987) 113-123, Schultz et al.
Molecular and Celluar Bio., Dec. 1983, 2156-2165, Smith et al.
Virology 170, 31-39 (1989) Luckow et al.
Vector development for filamentous fungi, van den Hondel et al.1-28, Apr. 1990.
Methods in Enzymology, vol. 71, 1981,McKeon et al., 275-281.
Methods in Enzymology, vol. 71, Lipids, Part C, 1981 178-180.
Stearoyl-Acyl Carrier Proten Desaturase from Safflower Seeds, McKeon et al., 275-281, Methods in Enzymology, vol. 71, 1981.
Annu.Rev.Plant Physiol. Plant Mol. Biol, 1991, 42:205-225, Gene Transfer to Plants.
Nucleic Acids Res., vol. 12, No. 22, 1984, Bevan.
Nucleic Acids Res., vol. 16, No. 20, 1988, Hoefgen.
Transgenic Plants, vol.1, Vectors for Gene Transfer in Higher Plants, White, 15-48.
Methods in Enzymology, vol. 185, Gottesman, 119-128.
Natl., Academy of Sci, Nov. 1997, vol. 74,No. 11, Nicklen et al., 5463-5467.
Nucleic Acids Res., vol. 13, No. 13, 1985, Bytebier et al.
Physiologia Plantarum, vol. XV, 1962,Murashige et al., 473-497.
J.PlantPhysiol., vol. 144, 265-271, 1994, Kohn et al.
Eur.J.Biochem.276,3801-3811, FEBS 2000, Sperling et al.
J.of Bio.Chem., vol. 273, No. 44, Oct. 30, 1998, 28590-28596, Sperling et al.
An Uncommon Pathway in the Biosynthesis of Acetylenic Fatty Acids in Mosses, Beutelmann et al., 546-548, 1995.
C.R.Acad.Sci. Paris, 1993,316: 1194-1199, Bechtold et al.
Maydica 42 (1997) 143-154, Pareddy et al.
The Plant Jrl., (1998) 13(1), 51-61, Pasentsis et al.
The Plant Jrl.,(1998) 15(1) : 39-48, Girke et al.
Biochimie (1994) 76,674-692,F. Lederer.
Biochemistry 1994, 33, 12787-12794, Shanklin et al.
Cell,vol. 21, 285-294,Aug. 1998, Guilley et al.
Plant,Jan. 1999, vol. 4, No. 1 [37] 1-14 issn 1360-1385.
Plant Science, 66(1990) 221-230, Hoefgen et al.
Apl.Mol.Genetics of Fungi, Gene Transfer Systems and Plant Physiology and Biochemistry, vol. 26, No. 1, Jan.-Feb. 1988, Wang et al., 777-792.
Biochemical Jrl., 1998, 330, Napier et al., 611-614.
Nucleic Acids Res., vol. 12, No. 1, 1984, Devereux et al., 387-395.
Jrl.Molecular Evolution, vol. 25, 1987, 225-260, Dams et al.
Computer Application in the Biosciences, vol. 5, 1989 ,Higgins et al., 151-153.
J.of Bio.Chem., vol. 265, No. 33, Nov. 25, 1990, 20144-20149, Stukey et al.
Nature Int. Weekly Jrl.of Sci., Enchancement of chilling tolerance . . . Wada et al., 200-203, vol. 347, Sep. 13, 1990.
Mol.GenGenet (1991) 225:459-467, Baeumlein et al.
EMBOJrl.. vol. 8, No. 9, 2445-2451, 1989,Stockhaus et al.
Plant Jrl. (1992) 2(3),397-404, Gatz et al.
Cloning ofΔ12-andΔ6-Desaturases from *Mortierella alpina* . . . , Huang et al, 649-659.

* cited by examiner

Fig. 1: Structure of expression cassettes
A) pBinAR
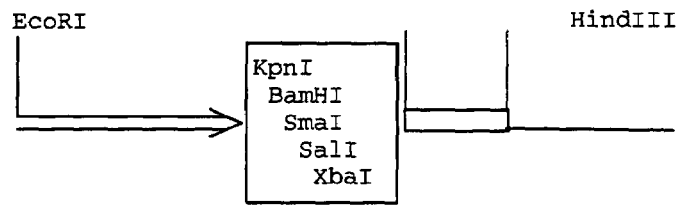
B) pBinUSP
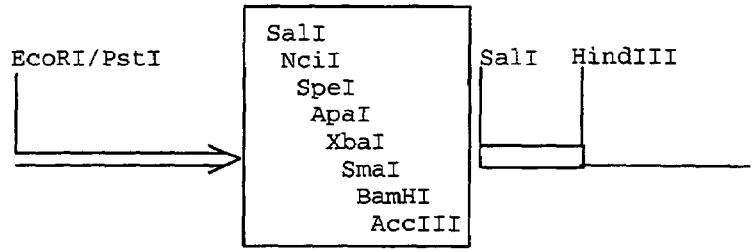
C) pBinARI
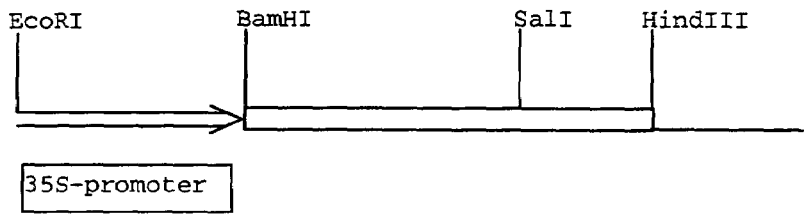
D) pBIN-USP Cer1
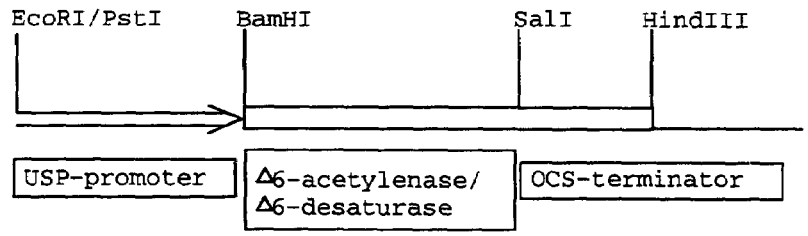
USP = unknown seed protein
35S = promoter from cauliflower terminator
OCS = octopine synthase terminator

SEQUENCE LISTING

<160> NUMBER OF SEQ ID NOS: 28

<210> SEQ ID NO 1
<211> LENGTH: 2040
<212> TYPE: DNA
<213> ORGANISM: Ceratodon purpureus
<220> FEATURE:
<221> NAME/KEY: CDS
<222> LOCATION: (176)..(1627)

<400> SEQUENCE: 1

```
ctcaggcagg tctcagttga tgagacgctg agttctgaat cctttgagct gtgtcaggct     60
cggcacttgt gggatggtga aggagtgatc gatcaggagt gcaggagctg cattagtttc    120
tcagggtcga tcaggttatt ctgaaaaagg ctgcgtctgt gagcagtttg caaaa atg     178
                                                              Met
                                                                1 gcc ctc gtt acc gac ttt ctg aac ttt ctg ggc acg aca tgg agc aag      226
Ala Leu Val Thr Asp Phe Leu Asn Phe Leu Gly Thr Thr Trp Ser Lys
        5                  10                  15 tac agc gtg tac acc cat agc tat gct gga aac tat ggg cct act ttg      274
Tyr Ser Val Tyr Thr His Ser Tyr Ala Gly Asn Tyr Gly Pro Thr Leu
         20                  25                  30 aag cac gcc aaa aag gtt tct gct caa ggt aaa act gcg gga cag aca      322
Lys His Ala Lys Lys Val Ser Ala Gln Gly Lys Thr Ala Gly Gln Thr
 35                  40                  45
```

-continued

| | |
|---|---|
| ctg aga cag aga tcg gtg cag gac aaa aag cca ggc act tac tct ctg<br>Leu Arg Gln Arg Ser Val Gln Asp Lys Lys Pro Gly Thr Tyr Ser Leu<br>50                         55                    60                      65 | 370 |
| gcc gat gtt gct tct cac gac agg cct gga gac tgc tgg atg atc gtc<br>Ala Asp Val Ala Ser His Asp Arg Pro Gly Asp Cys Trp Met Ile Val<br>                  70                        75                      80 | 418 |
| aaa gag aag gtg tat gat att agc cgt ttt gcg gac gac cac cct gga<br>Lys Glu Lys Val Tyr Asp Ile Ser Arg Phe Ala Asp Asp His Pro Gly<br>                    85                        90                      95 | 466 |
| ggg acg gta att agc acc tac ttt ggg cgg gat ggc aca gac gtt ttc<br>Gly Thr Val Ile Ser Thr Tyr Phe Gly Arg Asp Gly Thr Asp Val Phe<br>      100                    105                    110 | 514 |
| gca aca ttc cat cca cct gcc gca tgg aag caa ctc aat gac tac tac<br>Ala Thr Phe His Pro Pro Ala Ala Trp Lys Gln Leu Asn Asp Tyr Tyr<br>115                      120                    125 | 562 |
| att gga gac ctt gct agg gaa gag ccc ctt gat gaa ttg ctt aaa gac<br>Ile Gly Asp Leu Ala Arg Glu Glu Pro Leu Asp Glu Leu Leu Lys Asp<br>130                      135                    140                    145 | 610 |
| tac aga gat atg aga gcc gag ttt gtt aga gaa ggg ctt ttc aag agt<br>Tyr Arg Asp Met Arg Ala Glu Phe Val Arg Glu Gly Leu Phe Lys Ser<br>                150                    155                    160 | 658 |
| tcc aag gcc tgg ttc ctg ctt cag act ctg att aat gca gct ctc ttt<br>Ser Lys Ala Trp Phe Leu Leu Gln Thr Leu Ile Asn Ala Ala Leu Phe<br>                  165                    170                    175 | 706 |
| gct gcg agc att gcg act atc tgt tac gac aag agt tac tgg gct att<br>Ala Ala Ser Ile Ala Thr Ile Cys Tyr Asp Lys Ser Tyr Trp Ala Ile<br>180                      185                    190 | 754 |
| gtg ctg tca gcc agt ttg atg ggt ctc ttc gtc caa cag tgt gga tgg<br>Val Leu Ser Ala Ser Leu Met Gly Leu Phe Val Gln Gln Cys Gly Trp<br>      195                    200                    205 | 802 |
| ctt gcc cat gat ttc ctt cat caa cag gtc ttt gag aac cgt acc gcg<br>Leu Ala His Asp Phe Leu His Gln Gln Val Phe Glu Asn Arg Thr Ala<br>210                      215                    220                    225 | 850 |
| aac tcc ttc ttt ggc tat ttg ttc ggc aat tgc gtg ctt ggc ttt agt<br>Asn Ser Phe Phe Gly Tyr Leu Phe Gly Asn Cys Val Leu Gly Phe Ser<br>                  230                    235                    240 | 898 |
| gta tca tgg tgg agg acg aag cac aac att cat cat act gct ccg aat<br>Val Ser Trp Trp Arg Thr Lys His Asn Ile His His Thr Ala Pro Asn<br>                    245                    250                    255 | 946 |
| gag tgc gac gaa cag tac aca cct cta gac gaa gac att gat act ctc<br>Glu Cys Asp Glu Gln Tyr Thr Pro Leu Asp Glu Asp Ile Asp Thr Leu<br>      260                    265                    270 | 994 |
| ccc atc att gcc tgg agc aag gaa att ttg gcc acc gtt gag agc aag<br>Pro Ile Ile Ala Trp Ser Lys Glu Ile Leu Ala Thr Val Glu Ser Lys<br>275                      280                    285 | 1042 |
| aga att ttg cga gtg ctt caa tat cag cac tac atg att ctg cct cta<br>Arg Ile Leu Arg Val Leu Gln Tyr Gln His Tyr Met Ile Leu Pro Leu<br>290                      295                    300                    305 | 1090 |
| ttg ttc atg gcc cgg tac agt tgg act ttt gga agt ttg ctc ttc aca<br>Leu Phe Met Ala Arg Tyr Ser Trp Thr Phe Gly Ser Leu Leu Phe Thr<br>                310                    315                    320 | 1138 |
| ttc aat cct gat ttg agc acg acc aag gga ttg ata gag aag gga aca<br>Phe Asn Pro Asp Leu Ser Thr Thr Lys Gly Leu Ile Glu Lys Gly Thr<br>                  325                    330                    335 | 1186 |
| gtt gct ttt cac tac gcc tgg ttc agt tgg gct gcg ttc cat att ttg<br>Val Ala Phe His Tyr Ala Trp Phe Ser Trp Ala Ala Phe His Ile Leu<br>                    340                    345                    350 | 1234 |
| ccg ggt gtc gct aag cct ctt gcg tgg atg gta gca act gag ctt gtg<br>Pro Gly Val Ala Lys Pro Leu Ala Trp Met Val Ala Thr Glu Leu Val | 1282 |

|  |  |  |  |  |  |  |  |  |  |  |  |  |  |  |  |  |
|---|---|---|---|---|---|---|---|---|---|---|---|---|---|---|---|---|
|  | 355 |  |  |  |  | 360 |  |  |  |  | 365 |  |  |  |  |  |
| gcc | ggt | ttg | ttg | ttg | gga | ttc | gtg | ttt | acg | ttg | agt | cac | aat | gga | aag | 1330 |
| Ala | Gly | Leu | Leu | Leu | Gly | Phe | Val | Phe | Thr | Leu | Ser | His | Asn | Gly | Lys |  |
| 370 |  |  |  |  | 375 |  |  |  |  | 380 |  |  |  |  | 385 |  |
| gag | gtt | tac | aat | gaa | tcg | aag | gac | ttc | gtg | aga | gcc | cag | gtt | att | acc | 1378 |
| Glu | Val | Tyr | Asn | Glu | Ser | Lys | Asp | Phe | Val | Arg | Ala | Gln | Val | Ile | Thr |  |
|  |  |  |  |  | 390 |  |  |  |  | 395 |  |  |  |  | 400 |  |
| acc | cgt | aac | acc | aag | cga | ggc | tgg | ttc | aac | gat | tgg | ttc | act | ggg | gga | 1426 |
| Thr | Arg | Asn | Thr | Lys | Arg | Gly | Trp | Phe | Asn | Asp | Trp | Phe | Thr | Gly | Gly |  |
|  |  |  |  | 405 |  |  |  |  | 410 |  |  |  |  | 415 |  |  |
| ctc | gac | acc | cag | att | gag | cat | cac | ctg | ttt | cca | aca | atg | ccc | agg | cac | 1474 |
| Leu | Asp | Thr | Gln | Ile | Glu | His | His | Leu | Phe | Pro | Thr | Met | Pro | Arg | His |  |
|  |  |  | 420 |  |  |  |  | 425 |  |  |  |  | 430 |  |  |  |
| aac | tac | ccc | aag | atc | gca | cct | cag | gtc | gag | gct | ctt | tgc | aag | aag | cac | 1522 |
| Asn | Tyr | Pro | Lys | Ile | Ala | Pro | Gln | Val | Glu | Ala | Leu | Cys | Lys | Lys | His |  |
|  |  | 435 |  |  |  |  | 440 |  |  |  |  | 445 |  |  |  |  |
| ggc | ctc | gag | tac | gat | aat | gtc | tcc | gtc | gtt | ggt | gcc | tct | gtc | gcg | gtt | 1570 |
| Gly | Leu | Glu | Tyr | Asp | Asn | Val | Ser | Val | Val | Gly | Ala | Ser | Val | Ala | Val |  |
| 450 |  |  |  |  | 455 |  |  |  |  | 460 |  |  |  |  | 465 |  |
| gtg | aag | gcg | ctc | aag | gaa | att | gct | gat | gaa | gcg | tca | att | cgg | ctt | cac | 1618 |
| Val | Lys | Ala | Leu | Lys | Glu | Ile | Ala | Asp | Glu | Ala | Ser | Ile | Arg | Leu | His |  |
|  |  |  |  | 470 |  |  |  |  | 475 |  |  |  |  | 480 |  |  |
| gct | cac | taa | gaaatcgtcg | aactttgact | attcatttt | ttcgcctggc |  |  |  |  |  |  |  |  |  | 1667 |
| Ala | His |  |  |  |  |  |  |  |  |  |  |  |  |  |  |  |
| tacctcaaat | gttcgggagc | aggtgcttgg | cagtgtgttc | aaccggagcg | cactgaaaat |  |  |  |  |  |  |  |  |  |  | 1727 |
| gtgcagaatc | catttccaga | aattaccatt | cctagctaaa | tcttctttt | accaggtcgg |  |  |  |  |  |  |  |  |  |  | 1787 |
| atatatgaaa | cttttttgat | gcaacaagta | gcattcaatt | gaagacattg | ttcgagatat |  |  |  |  |  |  |  |  |  |  | 1847 |
| aattcgcagt | gtttctattc | agcgggcata | cgtactagtc | catatcggcg | gttgccgaga |  |  |  |  |  |  |  |  |  |  | 1907 |
| gtttacatta | ttagttggca | caacgagtag | atctagtgta | aatttctatt | tccgcatgta |  |  |  |  |  |  |  |  |  |  | 1967 |
| atattactct | gaatatatac | cgttatctat | tttcctaaaa | aaaaaaaaaa | aaaaaaaaaa |  |  |  |  |  |  |  |  |  |  | 2027 |
| aaaaaaaaaa | aaa |  |  |  |  |  |  |  |  |  |  |  |  |  |  | 2040 |

<210> SEQ ID NO 2
<211> LENGTH: 483
<212> TYPE: PRT
<213> ORGANISM: Ceratodon purpureus

<400> SEQUENCE: 2

Met Ala Leu Val Thr Asp Phe Leu Asn Phe Leu Gly Thr Thr Trp Ser
1               5                   10                  15

Lys Tyr Ser Val Tyr Thr His Ser Tyr Ala Gly Asn Tyr Gly Pro Thr
            20                  25                  30

Leu Lys His Ala Lys Lys Val Ser Ala Gln Gly Lys Thr Ala Gly Gln
        35                  40                  45

Thr Leu Arg Gln Arg Ser Val Gln Asp Lys Lys Pro Gly Thr Tyr Ser
    50                  55                  60

Leu Ala Asp Val Ala Ser His Asp Arg Pro Gly Asp Cys Trp Met Ile
65                  70                  75                  80

Val Lys Glu Lys Val Tyr Asp Ile Ser Arg Phe Ala Asp Asp His Pro
                85                  90                  95

Gly Gly Thr Val Ile Ser Thr Tyr Phe Gly Arg Asp Gly Thr Asp Val
            100                 105                 110

Phe Ala Thr Phe His Pro Pro Ala Ala Trp Lys Gln Leu Asn Asp Tyr
        115                 120                 125

```
Tyr Ile Gly Asp Leu Ala Arg Glu Pro Leu Asp Glu Leu Leu Lys
        130                 135                 140

Asp Tyr Arg Asp Met Arg Ala Glu Phe Val Arg Glu Gly Leu Phe Lys
145                 150                 155                 160

Ser Ser Lys Ala Trp Phe Leu Leu Gln Thr Leu Ile Asn Ala Ala Leu
                165                 170                 175

Phe Ala Ala Ser Ile Ala Thr Ile Cys Tyr Asp Lys Ser Tyr Trp Ala
            180                 185                 190

Ile Val Leu Ser Ala Ser Leu Met Gly Leu Phe Val Gln Gln Cys Gly
        195                 200                 205

Trp Leu Ala His Asp Phe Leu His Gln Gln Val Phe Glu Asn Arg Thr
    210                 215                 220

Ala Asn Ser Phe Phe Gly Tyr Leu Phe Gly Asn Cys Val Leu Gly Phe
225                 230                 235                 240

Ser Val Ser Trp Trp Arg Thr Lys His Asn Ile His His Thr Ala Pro
                245                 250                 255

Asn Glu Cys Asp Glu Gln Tyr Thr Pro Leu Asp Glu Asp Ile Asp Thr
            260                 265                 270

Leu Pro Ile Ile Ala Trp Ser Lys Glu Ile Leu Ala Thr Val Glu Ser
        275                 280                 285

Lys Arg Ile Leu Arg Val Leu Gln Tyr Gln His Tyr Met Ile Leu Pro
290                 295                 300

Leu Leu Phe Met Ala Arg Tyr Ser Trp Thr Phe Gly Ser Leu Leu Phe
305                 310                 315                 320

Thr Phe Asn Pro Asp Leu Ser Thr Thr Lys Gly Leu Ile Glu Lys Gly
                325                 330                 335

Thr Val Ala Phe His Tyr Ala Trp Phe Ser Trp Ala Ala Phe His Ile
            340                 345                 350

Leu Pro Gly Val Ala Lys Pro Leu Ala Trp Met Val Ala Thr Glu Leu
        355                 360                 365

Val Ala Gly Leu Leu Leu Gly Phe Val Phe Thr Leu Ser His Asn Gly
370                 375                 380

Lys Glu Val Tyr Asn Glu Ser Lys Asp Phe Val Arg Ala Gln Val Ile
385                 390                 395                 400

Thr Thr Arg Asn Thr Lys Arg Gly Trp Phe Asn Asp Trp Phe Thr Gly
                405                 410                 415

Gly Leu Asp Thr Gln Ile Glu His His Leu Phe Pro Thr Met Pro Arg
            420                 425                 430

His Asn Tyr Pro Lys Ile Ala Pro Gln Val Glu Ala Leu Cys Lys Lys
        435                 440                 445

His Gly Leu Glu Tyr Asp Asn Val Ser Val Gly Ala Ser Val Ala
450                 455                 460

Val Val Lys Ala Leu Lys Glu Ile Ala Asp Glu Ala Ser Ile Arg Leu
465                 470                 475                 480

His Ala His

<210> SEQ ID NO 3
<211> LENGTH: 1467
<212> TYPE: DNA
<213> ORGANISM: Ceratodon purpureus
<220> FEATURE:
<221> NAME/KEY: CDS
<222> LOCATION: (10)..(1461)

<400> SEQUENCE: 3
```

-continued

```
ggatccaaa atg gcc ctc gtt acc gac ttt ctg aac ttt ctg ggc acg aca        51
          Met Ala Leu Val Thr Asp Phe Leu Asn Phe Leu Gly Thr Thr
            1               5                  10 tgg agc aag tac agc gtg tac acc cat agc tat gct gga aac tat ggg         99
Trp Ser Lys Tyr Ser Val Tyr Thr His Ser Tyr Ala Gly Asn Tyr Gly
 15              20                  25                  30 cct act ttg aag cac gcc aaa aag gtt tct gct caa ggt aaa act gcg        147
Pro Thr Leu Lys His Ala Lys Lys Val Ser Ala Gln Gly Lys Thr Ala
                 35                  40                  45 gga cag aca ctg aga cag aga tcg gtg cag gac aaa aag cca ggc act        195
Gly Gln Thr Leu Arg Gln Arg Ser Val Gln Asp Lys Lys Pro Gly Thr
                 50                  55                  60 tac tct ctg gcc gat gtt gct tct cac gac agg cct gga gac tgc tgg        243
Tyr Ser Leu Ala Asp Val Ala Ser His Asp Arg Pro Gly Asp Cys Trp
         65                  70                  75 atc gtc aaa gag aag gtg tat gat att agc cgt ttt gcg gac gac            291
Met Ile Val Lys Glu Lys Val Tyr Asp Ile Ser Arg Phe Ala Asp Asp
     80                  85                  90 cac cct gga ggg acg gta att agc acc tac ttt ggg cgg gat ggc aca        339
His Pro Gly Gly Thr Val Ile Ser Thr Tyr Phe Gly Arg Asp Gly Thr
 95                 100                 105                 110 gac gtt ttc gca aca ttc cat cca cct gcc gca tgg aag caa ctc aat        387
Asp Val Phe Ala Thr Phe His Pro Pro Ala Ala Trp Lys Gln Leu Asn
                115                 120                 125 gac tac tac att gga gac ctt gct agg gaa gag ccc ctt gat gaa ttg        435
Asp Tyr Tyr Ile Gly Asp Leu Ala Arg Glu Glu Pro Leu Asp Glu Leu
                130                 135                 140 ctt aaa gac tac aga gat atg aga gcc gag ttt gtt aga gaa ggg ctt        483
Leu Lys Asp Tyr Arg Asp Met Arg Ala Glu Phe Val Arg Glu Gly Leu
            145                 150                 155 ttc aag agt tcc aag gcc tgg ttc ctg ctt cag act ctg att aat gca        531
Phe Lys Ser Ser Lys Ala Trp Phe Leu Leu Gln Thr Leu Ile Asn Ala
160                 165                 170 gct ctc ttt gct gcg agc att gcg act atc tgt tac gac aag agt tac        579
Ala Leu Phe Ala Ala Ser Ile Ala Thr Ile Cys Tyr Asp Lys Ser Tyr
175                 180                 185                 190 tgg gct att gtg ctg tca gcc agt ttg atg ggt ctc ttc gtc caa cag        627
Trp Ala Ile Val Leu Ser Ala Ser Leu Met Gly Leu Phe Val Gln Gln
                195                 200                 205 tgt gga tgg ctt gcc cat gat ttc ctt cat caa cag gtc ttt gag aac        675
Cys Gly Trp Leu Ala His Asp Phe Leu His Gln Gln Val Phe Glu Asn
            210                 215                 220 cgt acc gcg aac tcc ttc ttt ggc tat ttg ttc ggc aat tgc gtg ctt        723
Arg Thr Ala Asn Ser Phe Phe Gly Tyr Leu Phe Gly Asn Cys Val Leu
                225                 230                 235 ggc ttt agt gta tca tgg tgg agg acg aag cac aac att cat cat act        771
Gly Phe Ser Val Ser Trp Trp Arg Thr Lys His Asn Ile His His Thr
        240                 245                 250 gct ccg aat gag tgc gac gaa cag tac aca cct cta gac gaa gac att        819
Ala Pro Asn Glu Cys Asp Glu Gln Tyr Thr Pro Leu Asp Glu Asp Ile
255                 260                 265                 270 gat act ctc ccc atc att gcc tgg agc aag gaa att ttg gcc acc gtt        867
Asp Thr Leu Pro Ile Ile Ala Trp Ser Lys Glu Ile Leu Ala Thr Val
                275                 280                 285 gag agc aag aga att ttg cga gtg ctt caa tat cag cac tac atg att        915
Glu Ser Lys Arg Ile Leu Arg Val Leu Gln Tyr Gln His Tyr Met Ile
            290                 295                 300 ctg cct cta ttg ttc atg gcc cgg tac agt tgg act ttt gga agt ttg        963
Leu Pro Leu Leu Phe Met Ala Arg Tyr Ser Trp Thr Phe Gly Ser Leu
            305                 310                 315
```

-continued

```
ctc ttc aca ttc aat cct gat ttg agc acg acc aag gga ttg ata gag    1011
Leu Phe Thr Phe Asn Pro Asp Leu Ser Thr Thr Lys Gly Leu Ile Glu
320                 325                 330 aag gga aca gtt gct ttt cac tac gcc tgg ttc agt tgg gct gcg ttc    1059
Lys Gly Thr Val Ala Phe His Tyr Ala Trp Phe Ser Trp Ala Ala Phe
335                 340                 345                 350 cat att ttg ccg ggt gtc gct aag cct ctt gcg tgg atg gta gca act    1107
His Ile Leu Pro Gly Val Ala Lys Pro Leu Ala Trp Met Val Ala Thr
                355                 360                 365 gag ctt gtg gcc ggt ttg ttg ttg gga ttc gtg ttt acg ttg agt cac    1155
Glu Leu Val Ala Gly Leu Leu Leu Gly Phe Val Phe Thr Leu Ser His
370                 375                 380 aat gga aag gag gtt tac aat gaa tcg aag gac ttc gtg aga gcc cag    1203
Asn Gly Lys Glu Val Tyr Asn Glu Ser Lys Asp Phe Val Arg Ala Gln
385                 390                 395 gtt att acc acc cgt aac acc aag cga ggc tgg ttc aac gat tgg ttc    1251
Val Ile Thr Thr Arg Asn Thr Lys Arg Gly Trp Phe Asn Asp Trp Phe
400                 405                 410 act ggg gga ctc gac acc cag att gag cat cac ctg ttt cca aca atg    1299
Thr Gly Gly Leu Asp Thr Gln Ile Glu His His Leu Phe Pro Thr Met
415                 420                 425                 430 ccc agg cac aac tac ccc aag atc gca cct cag gtc gag gct ctt tgc    1347
Pro Arg His Asn Tyr Pro Lys Ile Ala Pro Gln Val Glu Ala Leu Cys
                435                 440                 445 aag aag cac ggc ctc gag tac gat aat gtc tcc gtc gtt ggt gcc tct    1395
Lys Lys His Gly Leu Glu Tyr Asp Asn Val Ser Val Val Gly Ala Ser
                450                 455                 460 gtc gcg gtt gtg aag gcg ctc aag gaa att gct gat gaa gcg tca att    1443
Val Ala Val Val Lys Ala Leu Lys Glu Ile Ala Asp Glu Ala Ser Ile
465                 470                 475 cgg ctt cac gct cac taa gtcgac                                     1467
Arg Leu His Ala His
   480
```

<210> SEQ ID NO 4
<211> LENGTH: 483
<212> TYPE: PRT
<213> ORGANISM: Ceratodon purpureus

<400> SEQUENCE: 4

```
Met Ala Leu Val Thr Asp Phe Leu Asn Phe Leu Gly Thr Thr Trp Ser
1               5                   10                  15

Lys Tyr Ser Val Tyr Thr His Ser Tyr Ala Gly Asn Tyr Gly Pro Thr
            20                  25                  30

Leu Lys His Ala Lys Lys Val Ser Ala Gln Gly Lys Thr Ala Gly Gln
        35                  40                  45

Thr Leu Arg Gln Arg Ser Val Gln Asp Lys Lys Pro Gly Thr Tyr Ser
    50                  55                  60

Leu Ala Asp Val Ala Ser His Asp Arg Pro Gly Asp Cys Trp Met Ile
65                  70                  75                  80

Val Lys Glu Lys Val Tyr Asp Ile Ser Arg Phe Ala Asp His Pro
                85                  90                  95

Gly Gly Thr Val Ile Ser Thr Tyr Phe Gly Arg Asp Gly Thr Asp Val
            100                 105                 110

Phe Ala Thr Phe His Pro Pro Ala Ala Trp Lys Gln Leu Asn Asp Tyr
        115                 120                 125

Tyr Ile Gly Asp Leu Ala Arg Glu Glu Pro Leu Asp Glu Leu Leu Lys
    130                 135                 140
```

Asp Tyr Arg Asp Met Arg Ala Glu Phe Val Arg Glu Gly Leu Phe Lys
145                 150                 155                 160

Ser Ser Lys Ala Trp Phe Leu Leu Gln Thr Leu Ile Asn Ala Ala Leu
            165                 170                 175

Phe Ala Ala Ser Ile Ala Thr Ile Cys Tyr Asp Lys Ser Tyr Trp Ala
        180                 185                 190

Ile Val Leu Ser Ala Ser Leu Met Gly Leu Phe Val Gln Gln Cys Gly
    195                 200                 205

Trp Leu Ala His Asp Phe Leu His Gln Gln Val Phe Glu Asn Arg Thr
210                 215                 220

Ala Asn Ser Phe Phe Gly Tyr Leu Phe Gly Asn Cys Val Leu Gly Phe
225                 230                 235                 240

Ser Val Ser Trp Trp Arg Thr Lys His Asn Ile His Thr Ala Pro
            245                 250                 255

Asn Glu Cys Asp Glu Gln Tyr Thr Pro Leu Asp Glu Asp Ile Asp Thr
        260                 265                 270

Leu Pro Ile Ile Ala Trp Ser Lys Glu Ile Leu Ala Thr Val Glu Ser
    275                 280                 285

Lys Arg Ile Leu Arg Val Leu Gln Tyr Gln His Tyr Met Ile Leu Pro
290                 295                 300

Leu Leu Phe Met Ala Arg Tyr Ser Trp Thr Phe Gly Ser Leu Leu Phe
305                 310                 315                 320

Thr Phe Asn Pro Asp Leu Ser Thr Thr Lys Gly Leu Ile Glu Lys Gly
            325                 330                 335

Thr Val Ala Phe His Tyr Ala Trp Phe Ser Trp Ala Ala Phe His Ile
        340                 345                 350

Leu Pro Gly Val Ala Lys Pro Leu Ala Trp Met Val Ala Thr Glu Leu
    355                 360                 365

Val Ala Gly Leu Leu Gly Phe Val Phe Thr Leu Ser His Asn Gly
370                 375                 380

Lys Glu Val Tyr Asn Glu Ser Lys Asp Phe Val Arg Ala Gln Val Ile
385                 390                 395                 400

Thr Thr Arg Asn Thr Lys Arg Gly Trp Phe Asn Asp Trp Phe Thr Gly
            405                 410                 415

Gly Leu Asp Thr Gln Ile Glu His His Leu Phe Pro Thr Met Pro Arg
        420                 425                 430

His Asn Tyr Pro Lys Ile Ala Pro Gln Val Glu Ala Leu Cys Lys Lys
    435                 440                 445

His Gly Leu Glu Tyr Asp Asn Val Ser Val Val Gly Ala Ser Val Ala
450                 455                 460

Val Val Lys Ala Leu Lys Glu Ile Ala Asp Glu Ala Ser Ile Arg Leu
465                 470                 475                 480

His Ala His

<210> SEQ ID NO 5
<211> LENGTH: 520
<212> TYPE: DNA
<213> ORGANISM: Ceratodon purpureus

<400> SEQUENCE: 5
cattcatcat actgctccga atgagtgcga cgaacagtac acacctctag acgaagacat    60
tgatactctc cccatcattg cctggagcaa ggaaattttg gccaccgttg agagcaagag   120
aattttgcga gtgcttcgat atcagcacta catgattctg cctctattgt tcatggcccg   180

```
gtacagttgg acttttggaa gtttgctctt cacattcaat cctgatttga gcacgaccaa    240
gggattgata gagaagggaa cagttgcttt tcactacgcc tggttcagtt gggctgcgtt    300
ccatattttg ccgggtgtcg ctaagcctct tgcgtggatg gtagcaactg agcttgtggc    360
cggtttgttg ttgggattcg tgtttacgtt gagtcacaat ggaaaggagg tttacaatga    420
atcgaaggac ttcgtgagag cccaggttat taccacccgt aacaccaagc gaggctggtt    480
caacgattgg ttcactgggg gactcgacac ccagattgag                          520
```

<210> SEQ ID NO 6
<211> LENGTH: 173
<212> TYPE: PRT
<213> ORGANISM: Ceratodon purpureus

<400> SEQUENCE: 6

```
Ile His His Thr Ala Pro Asn Glu Cys Asp Glu Gln Tyr Thr Pro Leu
  1               5                  10                  15

Asp Glu Asp Ile Asp Thr Leu Pro Ile Ile Ala Trp Ser Lys Glu Ile
             20                  25                  30

Leu Ala Thr Val Glu Ser Lys Arg Ile Leu Arg Val Gln Tyr Gln
         35                  40                  45

His Tyr Met Ile Leu Pro Leu Leu Phe Met Ala Arg Tyr Ser Trp Thr
     50                  55                  60

Phe Gly Ser Leu Leu Phe Thr Phe Asn Pro Asp Leu Ser Thr Thr Lys
 65                  70                  75                  80

Gly Leu Ile Glu Lys Gly Thr Val Ala Phe His Tyr Ala Trp Phe Ser
                 85                  90                  95

Trp Ala Ala Phe His Ile Leu Pro Gly Val Ala Lys Pro Leu Ala Trp
            100                 105                 110

Met Val Ala Thr Glu Leu Val Ala Gly Leu Leu Leu Gly Phe Val Phe
        115                 120                 125

Thr Leu Ser His Asn Gly Lys Glu Val Tyr Asn Glu Ser Lys Asp Phe
    130                 135                 140

Val Arg Ala Gln Val Ile Thr Thr Arg Asn Thr Lys Arg Gly Trp Phe
145                 150                 155                 160

Asn Asp Trp Phe Thr Gly Gly Leu Asp Thr Gln Ile Glu
                165                 170
```

<210> SEQ ID NO 7
<211> LENGTH: 514
<212> TYPE: DNA
<213> ORGANISM: Ceratodon purpureus

<400> SEQUENCE: 7

```
cctgcatcat gctgctccga atgaatgcga ccaaaagtac acgccgattg atgaggatat     60
tgatactctc cccatcattg cttggagtaa agatctcttg ccactgttg agagcaagac    120 catgttgcga gttcttcagt accagcacct attcttttg gttcttttga cgtttgcccg    180
ggcgagttgg ctattttgga gcgcggcctt cactctcagg cccgagttga cccttggcga    240 gaagctttg gagaggggaa cgatggcttt gcactacatt tggtttaata gtgttgcgtt    300
ttatctgctc cccggatgga aaccagttgt atggatggtg gtcagcgagc tcatgtctgg    360
tttcctgctg ggatacgtat ttgtactcag tcacaatgga atggaggtgt acaatacgtc    420
aaaggacttc gtgaatgccc agattgcatc gactcgcgac atcaaagcag gggtgtttaa    480
tgattggttc accggaggtc tcaacagaca gatt                                514
```

<210> SEQ ID NO 8
<211> LENGTH: 172
<212> TYPE: PRT
<213> ORGANISM: Ceratodon purpureus

<400> SEQUENCE: 8

```
Leu His His Ala Ala Pro Asn Glu Cys Asp Gln Lys Tyr Thr Pro Ile
  1               5                  10                  15

Asp Glu Asp Ile Asp Thr Leu Pro Ile Ile Ala Trp Ser Lys Asp Leu
             20                  25                  30

Leu Ala Thr Val Glu Ser Lys Thr Met Leu Arg Val Leu Gln Tyr Gln
         35                  40                  45

His Leu Phe Phe Leu Val Leu Leu Thr Phe Ala Arg Ala Ser Trp Leu
     50                  55                  60

Phe Trp Ser Ala Ala Phe Thr Leu Arg Pro Glu Leu Thr Leu Gly Glu
 65                  70                  75                  80

Lys Leu Leu Glu Arg Gly Thr Met Ala Leu His Tyr Ile Trp Phe Asn
                 85                  90                  95

Ser Val Ala Phe Tyr Leu Leu Pro Gly Trp Lys Pro Val Val Trp Met
            100                 105                 110

Val Val Ser Glu Leu Met Ser Gly Phe Leu Gly Tyr Val Phe Val
        115                 120                 125

Leu Ser His Asn Gly Met Glu Val Tyr Asn Thr Ser Lys Asp Phe Val
    130                 135                 140

Asn Ala Gln Ile Ala Ser Thr Arg Asp Ile Lys Ala Gly Val Phe Asn
145                 150                 155                 160

Asp Trp Phe Thr Gly Gly Leu Asn Arg Gln Ile Glu
                165                 170
```

<210> SEQ ID NO 9
<211> LENGTH: 535
<212> TYPE: DNA
<213> ORGANISM: Ceratodon purpureus

<400> SEQUENCE: 9

```
tgctcatcac atcgcctgta ataqtataga atatgatcca gacctacagt acatccccct      60
ttttgcagtg acatcaaagc tcttctctaa cctctactcc tacttctatg aaagggttat     120
gccattcgat ggcgtagcac gctctctgat tgcctaccag cactggacgt tttatccaat     180
aatggctgtt gctcgggtga acctctttgc ccaatccctt ctagtactga cctcgaagaa     240
gcatgtgcca gacaggtggc ttgagctcgg tgctatcggt ttcttctacc tgtggttctt     300
caccctcttg tcgtacctgc ccactgcacc ggagaggctg ctttcgtcc ttgtcagttt      360
tgcagtgaca gggatccagc atgtacagtt ttgcctgaac cacttctcat cgccggttta     420
tctaggacag ccgaagagca aggcttgggt tgaatctcaa gcacgggca ctctcaatct      480
ctctacaccg gcttacatgg attggtttca cggggtctt cagttccaga tcgag           535
```

<210> SEQ ID NO 10
<211> LENGTH: 178
<212> TYPE: PRT
<213> ORGANISM: Ceratodon purpureus

<400> SEQUENCE: 10

```
Ala His His Ile Ala Cys Asn Ser Ile Glu Tyr Asp Pro Asp Leu Gln
  1               5                  10                  15
```

-continued

```
Tyr Ile Pro Leu Phe Ala Val Thr Ser Lys Leu Phe Ser Asn Leu Tyr
         20                  25                  30
Ser Tyr Phe Tyr Glu Arg Val Met Pro Phe Asp Gly Val Ala Arg Ser
     35                  40                  45
Leu Ile Ala Tyr Gln His Trp Thr Phe Tyr Pro Ile Met Ala Val Ala
 50                  55                  60
Arg Val Asn Leu Phe Ala Gln Ser Leu Leu Val Leu Thr Ser Lys Lys
 65                  70                  75                  80
His Val Pro Asp Arg Trp Leu Glu Leu Gly Ala Ile Gly Phe Phe Tyr
                 85                  90                  95
Leu Trp Phe Phe Thr Leu Leu Ser Tyr Leu Pro Thr Ala Pro Glu Arg
             100                 105                 110
Leu Ala Phe Val Leu Val Ser Phe Ala Val Thr Gly Ile Gln His Val
             115                 120                 125
Gln Phe Cys Leu Asn His Phe Ser Ser Pro Val Tyr Leu Gly Gln Pro
     130                 135                 140
Lys Ser Lys Ala Trp Val Glu Ser Gln Ala Arg Gly Thr Leu Asn Leu
145                 150                 155                 160
Ser Thr Pro Ala Tyr Met Asp Trp Phe His Gly Gly Leu Gln Phe Gln
                165                 170                 175
Ile Glu
```

<210> SEQ ID NO 11
<211> LENGTH: 2160
<212> TYPE: DNA
<213> ORGANISM: Ceratodon purpureus
<220> FEATURE:
<221> NAME/KEY: CDS
<222> LOCATION: (159)..(1721)

<400> SEQUENCE: 11

```
cggaggtctc ttgtcgttct tggagtctgt gtcgagcttg aatgcggta ggcgcggccg      60 tttcgtggtt ttggcgttgg cattgcgcga gggcggacag tgggagtgcg ggaggtctgt    120
ttgtgcatga cgaggtggtt gtaatcttcg ccggcaga atg gtg tcc cag ggc ggc    176
                                            Met Val Ser Gln Gly Gly
                                             1               5 ggt ctc tcg cag ggt tcc att gaa gaa aac att gac gtt gag cac ttg      224
Gly Leu Ser Gln Gly Ser Ile Glu Glu Asn Ile Asp Val Glu His Leu
         10                  15                  20 gca acg atg ccc ctc gtc agt gac ttc cta aat gtc ctg gga acg act      272
Ala Thr Met Pro Leu Val Ser Asp Phe Leu Asn Val Leu Gly Thr Thr
     25                  30                  35 ttg ggc cag tgg agt ctt tcc act aca ttc gct ttc aag agg ctc acg      320
Leu Gly Gln Trp Ser Leu Ser Thr Thr Phe Ala Phe Lys Arg Leu Thr
 40                  45                  50 act aag aaa cac agt tcg gac atc tcg gtg gag gca caa aaa gaa tcg      368
Thr Lys Lys His Ser Ser Asp Ile Ser Val Glu Ala Gln Lys Glu Ser
 55                  60                  65                  70 gtt gcg cgg ggg cca gtt gag aat att tct caa tcg gtt gcg cag ccc      416
Val Ala Arg Gly Pro Val Glu Asn Ile Ser Gln Ser Val Ala Gln Pro
                 75                  80                  85 atc agg cgg agg tgg gtg cag gat aaa aag ccg gtt act tac agc ctg      464
Ile Arg Arg Arg Trp Val Gln Asp Lys Lys Pro Val Thr Tyr Ser Leu
             90                  95                 100 aag gat gta gct tcg cac gat atg ccc cag gac tgc tgg att ata atc      512
Lys Asp Val Ala Ser His Asp Met Pro Gln Asp Cys Trp Ile Ile Ile
             105                 110                 115
```

| | | | | | | | | | | | | | | |
|---|---|---|---|---|---|---|---|---|---|---|---|---|---|---|
| aaa | gag | aag | gtg | tat | gat | gtg | agc | acc | ttc | gct | gag | cag | cac | cct | gga | 560 |
| Lys | Glu | Lys | Val | Tyr | Asp | Val | Ser | Thr | Phe | Ala | Glu | Gln | His | Pro | Gly |
| | 120 | | | | 125 | | | | 130 | | | | | | | ggc acg gtt atc aac acc tac ttc gga cga gac gcc aca gat gtt ttc 608
Gly Thr Val Ile Asn Thr Tyr Phe Gly Arg Asp Ala Thr Asp Val Phe
135         140             145             150 tct act ttc cac gca tcc acc tca tgg aag att ctt cag aat ttc tac 656
Ser Thr Phe His Ala Ser Thr Ser Trp Lys Ile Leu Gln Asn Phe Tyr
            155             160             165 atc ggg aac ctt gtt agg gag gag ccg act ttg gag ctg ctg aag gag 704
Ile Gly Asn Leu Val Arg Glu Glu Pro Thr Leu Glu Leu Leu Lys Glu
        170             175             180 tac aga gag ttg aga gcc ctt ttc ttg aga gaa cag ctt ttc aag agt 752
Tyr Arg Glu Leu Arg Ala Leu Phe Leu Arg Glu Gln Leu Phe Lys Ser
    185             190             195 tcc aaa tcc tac tac ctt ttc aag act ctc ata aat gtt tcc att gtt 800
Ser Lys Ser Tyr Tyr Leu Phe Lys Thr Leu Ile Asn Val Ser Ile Val
200             205             210 gcc aca agc att gcg ata atc agt ctg tac aag tct tac cgg gcg gtt 848
Ala Thr Ser Ile Ala Ile Ile Ser Leu Tyr Lys Ser Tyr Arg Ala Val
215             220             225             230 ctg tta tca gcc agt ttg atg ggc ttg ttt att caa cag tgc gga tgg 896
Leu Leu Ser Ala Ser Leu Met Gly Leu Phe Ile Gln Gln Cys Gly Trp
            235             240             245 ttg tct cac gat ttt cta cac cat cag gta ttt gag aca cgc tgg ctc 944
Leu Ser His Asp Phe Leu His His Gln Val Phe Glu Thr Arg Trp Leu
        250             255             260 aat gac gtt gtt ggc tat gtg gtc ggc aac gtt gtt ctg gga ttc agt 992
Asn Asp Val Val Gly Tyr Val Val Gly Asn Val Val Leu Gly Phe Ser
    265             270             275 gtc tcg tgg tgg aag acc aag cac aac ctg cat cat gct gct ccg aat 1040
Val Ser Trp Trp Lys Thr Lys His Asn Leu His His Ala Ala Pro Asn
280             285             290 gaa tgc gac caa aag tac aca ccg att gat gag gat att gat act ctc 1088
Glu Cys Asp Gln Lys Tyr Thr Pro Ile Asp Glu Asp Ile Asp Thr Leu
295             300             305             310 ccc atc att gct tgg agt aaa gat ctc ttg gcc act gtt gag agc aag 1136
Pro Ile Ile Ala Trp Ser Lys Asp Leu Leu Ala Thr Val Glu Ser Lys
            315             320             325 acc atg ttg cga gtt ctt cag tac cag cac cta ttc ttt ttg gtt ctt 1184
Thr Met Leu Arg Val Leu Gln Tyr Gln His Leu Phe Phe Leu Val Leu
        330             335             340 ttg acg ttt gcc cgg gcg agt tgg cta ttt tgg agc gcg gcc ttc act 1232
Leu Thr Phe Ala Arg Ala Ser Trp Leu Phe Trp Ser Ala Ala Phe Thr
    345             350             355 ctc agg ccc gag ttg acc ctt ggc gag aag ctt ttg gag agg gga acg 1280
Leu Arg Pro Glu Leu Thr Leu Gly Glu Lys Leu Leu Glu Arg Gly Thr
360             365             370 atg gct ttg cac tac att tgg ttt aat agt gtt gcg ttt tat ctg ctc 1328
Met Ala Leu His Tyr Ile Trp Phe Asn Ser Val Ala Phe Tyr Leu Leu
375             380             385             390 ccc gga tgg aaa cca gtt gta tgg atg gtg gtc agc gag ctc atg tct 1376
Pro Gly Trp Lys Pro Val Val Trp Met Val Val Ser Glu Leu Met Ser
            395             400             405 ggt ttc ctg ctg gga tac gta ttt gta ctc agt cac aat gga atg gag 1424
Gly Phe Leu Leu Gly Tyr Val Phe Val Leu Ser His Asn Gly Met Glu
        410             415             420 gtg tac aat acg tca aag gac ttc gtg aat gcc cag att gca tcg act 1472
Val Tyr Asn Thr Ser Lys Asp Phe Val Asn Ala Gln Ile Ala Ser Thr
425             430             435

```
cgc gac atc aaa gca ggg gtg ttt aat gat tgg ttc acc gga ggt ctc      1520
Arg Asp Ile Lys Ala Gly Val Phe Asn Asp Trp Phe Thr Gly Gly Leu
    440                 445                 450 aac aga cag att gag cat cat cta ttt cca acg atg ccc agg cac aac      1568
Asn Arg Gln Ile Glu His His Leu Phe Pro Thr Met Pro Arg His Asn
455                 460                 465                 470 ctt aat aaa att tct cct cac gtg gag act ttg tgc aag aag cat gga      1616
Leu Asn Lys Ile Ser Pro His Val Glu Thr Leu Cys Lys Lys His Gly
                475                 480                 485 ctg gtc tac gaa gac gtg agc atg gct tcg ggc act tac cgg gtt ttg      1664
Leu Val Tyr Glu Asp Val Ser Met Ala Ser Gly Thr Tyr Arg Val Leu
            490                 495                 500 aaa aca ctt aag gac gtt gcc gat gct gct tca cac cag cag ctt gct      1712
Lys Thr Leu Lys Asp Val Ala Asp Ala Ala Ser His Gln Gln Leu Ala
        505                 510                 515 gcg agt tga ggcatcgcag cactcgtcga acattttg tctgttatag                1761
Ala Ser
    520 tgttcatatg tgatcgaggg gaaaaggtcc catgctctga tctattcttc tgtagccaat    1821
attttcaat tgaaaggagg ttcctcactt atcttccatc tatcgttgca catcctgcat     1881
cagagttagc gttggagtaa tgttaagcac ttgtagatta tgcccaccat tgccacattt    1941
ctgttcggtt acaatcgttt gattccatgc tatcctccgt gttcatctcg ttgttataag    2001
caagcttgaa aaacatgct acgagattgg cagacgttgt cttggcagct gtagaggttg     2061
gttccattca ttgtgtagta cagaactctc tcgtccctgt ttctctacat tacttgttac   2121
atagtgactt tcattcacag caaaaaaaaa aaaaaaaa                            2160
```

<210> SEQ ID NO 12
<211> LENGTH: 520
<212> TYPE: PRT
<213> ORGANISM: Ceratodon purpureus

<400> SEQUENCE: 12

```
Met Val Ser Gln Gly Gly Gly Leu Ser Gln Gly Ser Ile Glu Glu Asn
1               5                   10                  15

Ile Asp Val Glu His Leu Ala Thr Met Pro Leu Val Ser Asp Phe Leu
            20                  25                  30

Asn Val Leu Gly Thr Thr Leu Gly Gln Trp Ser Leu Ser Thr Thr Phe
        35                  40                  45

Ala Phe Lys Arg Leu Thr Lys Lys His Ser Ser Asp Ile Ser Val
    50                  55                  60

Glu Ala Gln Lys Glu Ser Val Ala Arg Gly Pro Val Glu Asn Ile Ser
65                  70                  75                  80

Gln Ser Val Ala Gln Pro Ile Arg Arg Trp Val Gln Asp Lys Lys
                85                  90                  95

Pro Val Thr Tyr Ser Leu Lys Asp Val Ala Ser His Asp Met Pro Gln
            100                 105                 110

Asp Cys Trp Ile Ile Ile Lys Glu Lys Val Tyr Asp Val Ser Thr Phe
        115                 120                 125

Ala Glu Gln His Pro Gly Gly Thr Val Ile Asn Thr Tyr Phe Gly Arg
    130                 135                 140

Asp Ala Thr Asp Val Phe Ser Thr Phe His Ala Ser Thr Ser Trp Lys
145                 150                 155                 160

Ile Leu Gln Asn Phe Tyr Ile Gly Asn Leu Val Arg Glu Glu Pro Thr
                165                 170                 175
```

-continued

```
Leu Glu Leu Leu Lys Glu Tyr Arg Glu Leu Arg Ala Leu Phe Leu Arg
            180                 185                 190

Glu Gln Leu Phe Lys Ser Ser Lys Ser Tyr Tyr Leu Phe Lys Thr Leu
        195                 200                 205

Ile Asn Val Ser Ile Val Ala Thr Ser Ile Ala Ile Ile Ser Leu Tyr
    210                 215                 220

Lys Ser Tyr Arg Ala Val Leu Leu Ser Ala Ser Leu Met Gly Leu Phe
225                 230                 235                 240

Ile Gln Gln Cys Gly Trp Leu Ser His Asp Phe Leu His His Gln Val
                245                 250                 255

Phe Glu Thr Arg Trp Leu Asn Asp Val Val Gly Tyr Val Val Gly Asn
            260                 265                 270

Val Val Leu Gly Phe Ser Val Ser Trp Trp Lys Thr Lys His Asn Leu
        275                 280                 285

His His Ala Ala Pro Asn Glu Cys Asp Gln Lys Tyr Thr Pro Ile Asp
    290                 295                 300

Glu Asp Ile Asp Thr Leu Pro Ile Ile Ala Trp Ser Lys Asp Leu Leu
305                 310                 315                 320

Ala Thr Val Glu Ser Lys Thr Met Leu Arg Val Leu Gln Tyr Gln His
                325                 330                 335

Leu Phe Phe Leu Val Leu Leu Thr Phe Ala Arg Ala Ser Trp Leu Phe
            340                 345                 350

Trp Ser Ala Ala Phe Thr Leu Arg Pro Glu Leu Thr Leu Gly Glu Lys
        355                 360                 365

Leu Leu Glu Arg Gly Thr Met Ala Leu His Tyr Ile Trp Phe Asn Ser
    370                 375                 380

Val Ala Phe Tyr Leu Leu Pro Gly Trp Lys Pro Val Val Trp Met Val
385                 390                 395                 400

Val Ser Glu Leu Met Ser Gly Phe Leu Gly Tyr Val Phe Val Leu
                405                 410                 415

Ser His Asn Gly Met Glu Val Tyr Asn Thr Ser Lys Asp Phe Val Asn
            420                 425                 430

Ala Gln Ile Ala Ser Thr Arg Asp Ile Lys Ala Gly Val Phe Asn Asp
        435                 440                 445

Trp Phe Thr Gly Gly Leu Asn Arg Gln Ile Glu His His Leu Phe Pro
    450                 455                 460

Thr Met Pro Arg His Asn Leu Asn Lys Ile Ser Pro His Val Glu Thr
465                 470                 475                 480

Leu Cys Lys Lys His Gly Leu Val Tyr Glu Asp Val Ser Met Ala Ser
                485                 490                 495

Gly Thr Tyr Arg Val Leu Lys Thr Leu Lys Asp Val Ala Asp Ala Ala
            500                 505                 510

Ser His Gln Gln Leu Ala Ala Ser
        515                 520

<210> SEQ ID NO 13
<211> LENGTH: 20
<212> TYPE: DNA
<213> ORGANISM: artificial sequence
<220> FEATURE:
<221> NAME/KEY: modified_base
<222> LOCATION: 15
<223> OTHER INFORMATION: 15 is inosine

<400> SEQUENCE: 13
```

```
tggtggaart ggamncayaa                                              20

<210> SEQ ID NO 14
<211> LENGTH: 20
<212> TYPE: DNA
<213> ORGANISM: artificial sequence
<220> FEATURE:
<221> NAME/KEY: modified_base
<222> LOCATION: 3, 12, 15
<223> OTHER INFORMATION: 3, 12, 15 are inosine

<400> SEQUENCE: 14
kgntggaark rnmancayaa                                              20

<210> SEQ ID NO 15
<211> LENGTH: 20
<212> TYPE: DNA
<213> ORGANISM: artificial sequence
<220> FEATURE:
<221> NAME/KEY: 3, 6, 12
<222> LOCATION: 3, 6, 12 are any nucleotide
<223> OTHER INFORMATION: sequencing primer

<400> SEQUENCE: 15
atntknggra anarrtgrtg                                              20

<210> SEQ ID NO 16
<211> LENGTH: 18
<212> TYPE: DNA
<213> ORGANISM: artificial sequence
<220> FEATURE:
<223> OTHER INFORMATION: sequencing primer

<400> SEQUENCE: 16
cgaatgagtg cgacgaac                                                18

<210> SEQ ID NO 17
<211> LENGTH: 18
<212> TYPE: DNA
<213> ORGANISM: artificial sequence
<220> FEATURE:
<223> OTHER INFORMATION: sequencing primer

<400> SEQUENCE: 17
aataacctgg gctctcac                                                18

<210> SEQ ID NO 18
<211> LENGTH: 20
<212> TYPE: DNA
<213> ORGANISM: artificial sequence
<220> FEATURE:
<223> OTHER INFORMATION: sequencing primer

<400> SEQUENCE: 18
atgaggatat tgatactctc                                              20

<210> SEQ ID NO 19
<211> LENGTH: 18
<212> TYPE: DNA
<213> ORGANISM: artificial sequence
<220> FEATURE:
<223> OTHER INFORMATION: sequencing primer

<400> SEQUENCE: 19
gcaatctggg cattcacg                                                18
```

<210> SEQ ID NO 20
<211> LENGTH: 18
<212> TYPE: DNA
<213> ORGANISM: artificial sequence
<220> FEATURE:
<223> OTHER INFORMATION: sequencing primer

<400> SEQUENCE: 20
gacatcaaag ctcttctc                                          18

<210> SEQ ID NO 21
<211> LENGTH: 18
<212> TYPE: DNA
<213> ORGANISM: artificial sequence
<220> FEATURE:
<223> OTHER INFORMATION: sequencing primer

<400> SEQUENCE: 21 ggcgatgag aagtggttc                                          18

<210> SEQ ID NO 22
<211> LENGTH: 26
<212> TYPE: DNA
<213> ORGANISM: artificial sequence
<220> FEATURE:
<223> OTHER INFORMATION: sequencing primer

<400> SEQUENCE: 22
ccggtaccat ggccctcgtt accgac                                 26

<210> SEQ ID NO 23
<211> LENGTH: 26
<212> TYPE: DNA
<213> ORGANISM: artificial sequence
<220> FEATURE:
<223> OTHER INFORMATION: sequencing primer

<400> SEQUENCE: 23
ccgaattctt agtgagcgtg aagccg                                 26

<210> SEQ ID NO 24
<211> LENGTH: 26
<212> TYPE: DNA
<213> ORGANISM: artificial sequence
<220> FEATURE:
<223> OTHER INFORMATION: sequencing primer

<400> SEQUENCE: 24
ccggtaccat ggtgtcccag ggcggc                                 26

<210> SEQ ID NO 25
<211> LENGTH: 26
<212> TYPE: DNA
<213> ORGANISM: artificial sequence
<220> FEATURE:
<223> OTHER INFORMATION: sequencing primer

<400> SEQUENCE: 25
ccgaattctc aactcgcagc aagctg                                 26

<210> SEQ ID NO 26
<211> LENGTH: 31
<212> TYPE: DNA
<213> ORGANISM: artificial sequence
<220> FEATURE:
<223> OTHER INFORMATION: sequencing primer

```
-continued

<400> SEQUENCE: 26
aaaaggatcc aaaatggccc tcgttaccga c                            31

<210> SEQ ID NO 27
<211> LENGTH: 27
<212> TYPE: DNA
<213> ORGANISM: artificial sequence
<220> FEATURE:
<223> OTHER INFORMATION: sequencing primer

<400> SEQUENCE: 27
aaaagtcgac ttagtgagcg tgaagcc                                 27

<210> SEQ ID NO 28
<211> LENGTH: 60
<212> TYPE: DNA
<213> ORGANISM: artificial sequence
<220> FEATURE:
<223> OTHER INFORMATION: sequencing primer

<400> SEQUENCE: 28 gtcgaccgc ggactagtgg gccctctaga cccgggggat ccggatctgc tggctatgaa    60
```

Δ6 ACETYLENASE AND Δ6-DESATURASE FROM CERATODON PURPUREUS

The present invention relates to a process for preparing unsaturated fatty acids and to a process for preparing triglycerides with an increased content of unsaturated fatty acids. The invention further relates to the use of DNA sequences coding for Δ6-acetylenase/Δ6-desaturases or Δ6-desaturases for producing a transgenic organism, preferably a transgenic plant or a transgenic microorganism with increased content of fatty acids, oils or lipids with Δ6 triple bonds and/or Δ6 double bonds.

The invention additionally relates to an isolated nucleic acid sequence; to an expression cassette comprising a nucleic acid sequence, a vector and organisms comprising at least one nucleic acid sequence or expression cassette. The invention additionally relates to unsaturated fatty acids and triglycerides with an increased content of unsaturated fatty acids and the use thereof.

Fatty acids and triglycerides have a large number of uses in the food industry, in livestock nutrition, in cosmetics and in the drugs sector. They are suitable for a wide variety of uses depending on whether they are free saturated or unsaturated fatty acids or triglycerides with an increased content of saturated or unsaturated fatty acids; thus, for example, polyunsaturated fatty acids are added to baby food to increase the nutritional value. The various fatty acids and triglycerides are mainly obtained from microorganisms such as mortierella or from oil-producing plants such as soybean, oilseed rape, sunflower and others, usually resulting in the form of their triglycerides. However, they can also be obtained from animal species such as fish. The free fatty acids are advantageously prepared by saponification.

Depending on the purpose of use, oils with saturated or unsaturated fatty acids are preferred; thus, for example, lipids with unsaturated fatty acids, specifically polyunsaturated fatty acids, are preferred in human nutrition because they have a beneficial effect on the blood cholesterol level and thus on the possibility of having heart disease. They are used in various dietetic human foods or medicines.

Because of their beneficial properties, there has in the past been no lack of approaches to making available the genes involved in the synthesis of fatty acids and triglycerides for producing oils in various organisms with an altered content of unsaturated fatty acids. Thus, WO 91/13972 and its US equivalent describe a Δ9-desaturase. WO 93/11245 claims a Δ15-desaturase, and WO 94/11516 claims a Δ12-desaturase. Δ6-Desaturases are described in WO 93/06712, U.S. Pat. No. 5,614,393, WO 96/21022 and WO 99/27111. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144–21049, Wada et al., Nature 347, 1990: 200–203 or Huang et al., Lipids 34, 1999: 649–659. WO 96/13591 describes and claims a Δ6-palmitoyl-ACP-desaturase. The biochemical characterization of the various desaturases is, however, to date inadequate because the enzymes can, as membrane-bound proteins, be isolated and characterized only with great difficulty (McKeon et al., Methods in Enzymol. 71, 1981: 12141–12147, Wang et al., Plant Physiol. Biochem., 26, 1988: 777–792).

WO 97/37033 describes a Δ12-acetylenase. This enzyme can be used to prepare unsaturated $C_{18}$-fatty acids with a triple bond. Besides the use in human foods, fatty acids of this type can also, because of their reactivity, be used to prepare polymers. Sperling et al. reported at a meeting (South Lake Tahoe, Canada, Jun. 9–13, 1999) on the cloning of an enzyme which likewise introduces triple bonds into fatty acids, but the substrates of this enzyme differ from those of the Δ12-acetylenase, and the triple bond is introduced into a different position in the fatty acids by the enzyme.

It was possible to demonstrate in yeasts both a shift in the fatty acid spectrum toward unsaturated fatty acids, and an increase in the productivity (see Huang et al., Lipids 34, 1999: 649–659, Napier et al., Biochem. J., Vol. 330, 1998: 611–614). However, expression of the various desaturases in transgenic plants did not show the required result. It was possible to show a shift in the fatty acid spectrum toward unsaturated fatty acids, but it emerged at the same time that there was a great diminution in the synthetic performance of the transgenic plants, that is to say only small amounts of oils could be isolated by comparison with the initial plants.

There is thus still a great need for novel genes which code for enzymes which are involved in the biosynthesis of unsaturated fatty acids and make it possible to prepare the latter on an industrial scale.

It is an object of the present invention to provide further enzymes for the synthesis of conjugated unsaturated fatty acids.

We have found that this object is achieved by an isolated nucleic acid sequence which codes for a polypeptide having Δ6-acetylenase and/or Δ6-desaturase activity, selected from the group:

a) of a nucleic acid sequence having the sequence depicted in SEQ ID NO: 1, SEQ ID NO: 3 or SEQ ID NO: 11.

b) nucleic acid sequences which, as a result of the degeneracy of the genetic code, are derived from the nucleic acid sequence depicted in SEQ ID NO: 1, SEQ ID NO: 3 or SEQ ID NO: 11, c) derivatives of the nucleic acid sequence depicted in SEQ ID NO: 1, SEQ ID NO: 3 or SEQ ID NO: 11, which code for polypeptides having the amino acid sequences depicted in SEQ ID NO: 2, and having at least 75% homology at the amino acid level with a negligible reduction in the enzymatic action of the polypeptides.

Derivative(s) mean, for example, functional homologs of the enzymes encoded by SEQ ID NO: 1, SEQ ID NO: 3 or SEQ ID NO: 11, or of their enzymatic activity, that is to say enzymes which catalyze the same enzymatic reactions as the enzymes encoded by SEQ ID NO: 1, SEQ ID NO: 3 or SEQ ID NO: 11. These genes likewise make it possible advantageously to prepare unsaturated fatty acids with triple bonds and/or double bonds in position 6. Unsaturated fatty acids mean hereinafter fatty acids with one or more unsaturations and with triple bonds and/or double bonds. The triple and/or double bonds may be conjugated or unconjugated. The sequences specified in SEQ ID NO: 1, SEQ ID NO: 3 or SEQ ID NO: 11 code for novel enzymes having acetylenase and/or Δ6-desaturase activity.

The novel enzyme Δ6-acetylenase/Δ6-desaturase advantageously introduces a cis double bond in position $C_6$–$C_7$ into fatty acid residues of glycerolipids and/or converts an already existing cis double bond in position $C_6$–$C_7$ into a triple bond (see SEQ ID NO: 1 or SEQ ID NO: 3). Furthermore, the enzyme has $\Delta^6$-desaturase activity which advantageously exclusively introduces a cis double bond in position $C_6$–$C_7$ into fatty acid residues of glycerolipids. The enzyme having the sequence specified in SEQ ID NO: 11 also has this activity and is a monofunctional Δ6-desaturase.

The novel nucleic acid sequence(s) (the singular is intended to include the plural, and vice versa, for the application) or fragments thereof can be used advantageously for isolating further genomic sequences by homology screening.

The derivatives mentioned can be isolated, for example, from other organisms, e.g. eukaryotic organisms such as plants such as, specifically, mosses, dinoflagellates or fungi.

In addition, derivatives or functional derivatives of the sequences specified in SEQ ID NO: 1, SEQ ID NO: 3 or SEQ ID NO: 11 mean, for example, allelic variants which, at the derived amino acid level, have at least 70% homology, advantageously at least 75% homology, preferably at least 80% homology, particularly preferably at least 85% homology, and very particularly preferably 90% homology. The homology has been calculated over the entire amino acid region. The program PileUp, BESTFIT, GAP, TRANSLATE or BACKTRANSLATE (=constituent of the UWGCG program package, Wisconsin Package, Version 10.0-UNIX, January 1999, Genetics Computer Group, Inc., Devereux et al., Nucleic Acids Res., 12, 1984: 387–395) was used (J. Mol. Evolution., 25, 351–350, 1987, Higgins et al., CABIOS, 5 1989: 151–153). The amino acid sequences derived from the specified nucleic acids are to be found in sequence SEQ ID NO: 2, SEQ ID NO: 4 and SEQ ID NO: 12. Homology means identity, that is to say the amino acid sequences are at least 70% identical. The novel sequences show at the nucleic acid level at least 65% homology, preferably at least 70%, particularly preferably 75%, very particularly preferably at least 80%.

Allelic variants comprise in particular functional variants which are obtainable from the sequence depicted in SEQ ID NO: 1, SEQ ID NO: 3 or SEQ ID NO: 11 by deletion, insertion or substitution of nucleotides, with retention of the enzymatic activity of the derived synthesized proteins.

Such DNA sequences can be isolated starting from the DNA sequences described in SEQ ID NO: 1, SEQ ID NO: 3 or SEQ ID NO: 11, or parts of these sequences, for example using conventional hybridization methods or the PCR technique, from other eukaryotes such as, for example, those mentioned above. These DNA sequences hybridize under standard conditions with the sequences mentioned. It is advantageous to use for the hybridization short oligonucleotides, for example of the conserved regions, which can be determined in a manner known to the skilled worker by comparisons with other acetylenase and/or desaturase genes. The histidine box sequences are advantageously used. However, it is also possible to use longer fragments of the novel nucleic acids or the complete sequences for the hybridization. These standard conditions vary depending on the nucleic acid used: oligonucleotide, longer fragment or complete sequence or depending on which type of nucleic acid, DNA or RNA, is used for the hybridization. Thus, for example, the melting temperatures for DNA:DNA hybrids are about 10° C. lower than those for DNA:RNA hybrids of the same length.

Standard conditions mean, for example, depending on the nucleic acid, temperatures between 42 and 58° C. in an aqueous buffer solution with a concentration between 0.1 and 5×SSC (1×SSC=0.15 M NaCl, 15 mM sodium citrate, pH 7.2) or additionally in the presence of 50% formamide, such as, for example, 42° C. in 5×SSC, 50% formamide. The hybridization conditions for DNA:DNA hybrids are advantageously 0.1×SSC and temperatures between about 20° C. and 45° C., preferably between about 30° C. and 45° C. The hybridization conditions for DNA:RNA hybrids are advantageously 0.1×SSC and temperatures between about 30° C. and 55° C., preferably between about 45° C. and 55° C. These temperatures stated for the hybridization are melting temperatures calculated by way of example for a nucleic acid with a length of about 100 nucleotides and a G+C content of 50% in the absence of formamide. The experimental conditions for DNA hybridization are described in relevant textbooks of genetics such as, for example, Sambrook et al., "Molecular Cloning", Cold Spring Harbor Laboratory, 1989, and can be calculated by the formulae known to the skilled worker, for example depending on the length of the nucleic acids, the nature of the hybrids or the G+C content. Further information on hybridization can be found by the skilled worker in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

Derivatives also mean homologs of the sequence SEQ ID NO: 1, SEQ ID NO: 3 or SEQ ID NO: 11, for example eukaryotic homologs, truncated sequences, single-stranded DNA of the coding and noncoding DNA sequence or RNA of the coding and noncoding DNA sequence.

In addition, homologs of sequences SEQ ID NO: 1, SEQ ID NO: 3 or SEQ ID NO: 11 mean derivatives such as, for example, promoter variants. These variants can be modified by one or more nucleotide exchanges, by insertion(s) and/or deletion(s) without, however, impairing the functionality or efficacy of the promoters. The promoters may moreover have their efficacy increased by modification of their sequence, or be completely replaced by more effective promoters even from heterologous organisms.

Derivatives also advantageously mean variants whose nucleotide sequence in the region from −1 to −2000 in front of the start codon has been modified so that gene expression and/or protein expression is altered, preferably increased. Derivatives also mean variants modified at the 3' end.

Derivatives also mean antisense DNAs which can be used to inhibit the biosynthesis of the novel proteins. These antisense DNAs are among the novel nonfunctional derivatives such as derivatives having no enzymatic activity. Further methods known to the skilled worker for producing nonfunctional derivatives are so-called cosuppression, the use of ribozymes and introns. Ribozymes are catalytic RNA molecules with ribonuclease activity able to cut single-stranded nucleic acids such as mRNA, to which they show a complementarity. This makes it possible by using these ribozymes (Haselhoff and Gerlach, Nature, 334, 1988: 585–591) to cleave mRNA transcripts catalytically, and thus suppress translation of this mRNA. Ribozymes of this type can be tailored specifically for their tasks (U.S. Pat. No. 4,987,071; U.S. Pat. No. 5,116,742 and Bartel et al., Science 261, 1993: 1411–1418). It is thus possible by use of antisense DNA to prepare fatty acids, lipids or oils with an increased content of saturated fatty acids.

The novel nucleic acid sequences which code for a Δ6-acetylenase/Δ6-desaturase and/or Δ6-desaturase can be prepared by synthesis or isolated from nature or comprise a mixture of synthetic and natural DNA constituents, and consist of various heterologous Δ6-acetylenase/Δ6-desaturase and/or Δ6-desaturase gene sections from various organisms. In general, synthetic nucleotide sequences are produced using codons which are preferred by the appropriate host organisms, for example plants. This usually results in optimal expression of the heterologous genes. The plant-preferred codons may be determined from codons with the greatest protein frequency which are expressed in most plant species of interest. One example for *Corynebacterium*

*glutamicum* is given in: Wada et al. (1992) *Nucleic Acids Res.* 20:2111–2118. Experiments of this type can be carried out by standard methods known to those skilled in the art.

Functionally equivalent sequences coding for the Δ6-acetylenase/Δ6-desaturase and/or Δ6-desaturase gene are those derivatives of the novel sequences which, despite a different nucleotide sequence, still have the required functions, that is to say the enzymatic activity of the proteins. Functional equivalents thus comprise naturally occurring variants of the sequences described herein, and artificial nucleotide sequences, for example obtained by chemical synthesis and adapted to the codon usage of a plant.

In addition, artificial DNA sequences are suitable as long as they confer, as described above, the required property, for example the increase in the content of Δ6 triple bonds or Δ6 double bonds in fatty acids, oils or lipids in the plant by overexpression of the Δ6-acetylenase/Δ6-desaturase and/or Δ6-desaturase gene in crop plants. Such artificial DNA sequences can be established, for example, by backtranslation by means of molecular modeling of constructed proteins which have Δ6-acetylenase/Δ6-desaturase and/or Δ6-desaturase activity or by in vitro selection. Possible techniques for in vitro evolution of DNA for modifying or improving DNA sequences are described in Patten, P. A. et al., Current Opinion in Biotechnology 8, 724–733 (1997) or in Moore, J. C. et al., Journal of Molecular Biology 272, 336–347 (1997). Coding DNA sequences which have been obtained by backtranslation of a polypeptide sequence complying with the codon usage specific for the host plant are particularly suitable. The specific codon usage can easily be established by a skilled worker familiar with methods of plant genetics by computer analyses of other, known genes in the plant to be transformed.

Further suitable equivalent nucleic acid sequences which should be mentioned are sequences which code for fusion proteins, where a Δ6-acetylenase/Δ6-desaturase and/or Δ6-desaturase polypeptide or a functional equivalent part thereof is a constituent of the fusion protein. The second part of the fusion protein can be, for example, another polypeptide with enzymatic activity or an antigenic polypeptide sequence with whose aid it is possible to detect Δ6-acetylenase/Δ6-desaturase and/or Δ6-desaturase expression (e.g. myc tag or his tag). However, this is preferably a regulatory protein sequence such as, for example, a signal sequence for the ER, which guides the Δ6-acetylenase/Δ6-desaturase and/or Δ6-desaturase protein to the required site of action.

It may be advantageous to combine the Δ6-acetylenase/Δ6-desaturase or Δ6-desaturase genes in the novel process with other genes of fatty acid biosynthesis. Examples of such genes are the acetyltransferases, other desaturases or elongases. Advantageous for in vitro and specifically in vitro synthesis is combination with, for example, NADH cytochrome B5 reductases, which are able to take up or release reducing equivalents.

The novel amino acid sequences mean proteins which comprise an amino acid sequence depicted in sequences SEQ ID NO: 2, SEQ ID NO: 4 or SEQ ID NO: 12, or a sequence obtainable therefrom by substitution, inversion, insertion or deletion of one or more amino acid residues, with the enzymatic activity of the protein represented in SEQ ID NO: 2, SEQ ID NO: 4 or SEQ ID NO: 12 being retained or negligibly reduced. Negligibly reduced means all enzymes which still have at least 10%, preferably 20%, particularly preferably 30%, of the enzymatic activity of the initial enzyme. It is moreover possible, for example, to replace particular amino acids by those having similar physicochemical properties (bulk, basicity, hydrophobicity etc.). For example, arginine residues are replaced by lysine residues, valine residues by isoleucine residues or aspartic acid residues by glutamic acid residues. However, it is also possible for one or more amino acids to be transposed in their sequence, added or deleted, or several of these measures can be combined together.

Derivatives also mean functional equivalents which comprise, in particular, also natural or artificial mutations of an originally isolated sequence coding for a Δ6-acetylenase/Δ6-desaturase and/or Δ6-desaturase and which additionally show the required function, that is to say the enzymatic activity is negligibly reduced. Mutations comprise substitutions, additions, deletions, transpositions or insertions of one or more nucleotide residues. Thus, for example, the present invention also comprises those nucleotide sequences which are obtained by modification of the Δ6-acetylenase/Δ6-desaturase and/or Δ6-desaturase nucleotide sequence. The aim of such a modification may be, for example, to localize further the coding sequence contained therein or, for example, also to insert further restriction enzyme cleavage sites.

Functional equivalents are also those variants whose function is, compared with the initial gene or gene fragment, attenuated (=negligibly reduced) or enhanced (=enzyme activity greater than the activity of the initial enzyme, that is to say the activity is over 100%, preferably over 110%, particularly preferably over 130%).

The nucleic acid sequence can moreover advantageously be, for example, a DNA or cDNA sequence. Coding sequences suitable for insertion into a novel expression cassette are, for example, those which code for a Δ6-acetylenase/Δ6-desaturase and/or Δ6-desaturase having the sequences described above and which confer on the host the ability to overproduce fatty acids, oils or lipids with triple bonds and/or double bonds in position 6. These sequences may be of homologous or heterologous origin.

The novel expression cassette (=nucleic acid construct or fragment) means the sequences which are specified in SEQ ID NO: 1, SEQ ID NO: 3 or SEQ ID NO: 11 and which result from the genetic code and/or their functional or nonfunctional derivatives which advantageously have been functionally linked to one or more regulatory signals to increase gene expression and which control the expression of the coding sequence in the host cell. These regulatory sequences are intended to make specific expression of the genes and protein expression possible. This may mean, for example, depending on the host organism that the gene is expressed and/or overexpressed only after induction, or that it is expressed and/or overexpressed immediately. For example, these regulatory sequences are sequences to which inducers or repressors bind and thus regulate the expression of the nucleic acid. In addition to these novel regulatory sequences or in place of these sequences, it is possible for the natural regulation of these sequences still to be present in front of the actual structural genes and, where appropriate, to have been genetically modified so that the natural regulation has been switched off and the expression of the genes has been increased. However, the gene construct may also have a simpler structure, that is to say no additional regulatory signals have been inserted in front of the nucleic acid sequence or its derivatives, and the natural promoter with its regulation has not been deleted. Instead, the natural regulatory sequence has been mutated so that regulation no longer takes place and/or gene expression is increased. These modified promoters may also be placed alone in the form of part sequences (=promoter with parts of the novel nucleic acid sequences) in front of the natural gene to increase the activity. In addition, the gene construct may advantageously comprise one or more so-called enhancer sequences functionally linked to the promoter, which make increased expression of the nucleic acid sequence possible. It is also possible to insert additional advantageous sequences at the 3' end of the DNA sequences, such as further regulatory elements or terminators. The Δ6-acetylenase/Δ6-desaturase and/or Δ6-desaturase genes may be present in one or more copies in the expression cassette (=gene construct).

The regulatory sequences or factors may moreover, as described above, preferably have a beneficial influence on expression of the inserted genes, and thus increase it. Thus, enhancement of regulatory elements can advantageously take place at the level of transcription by using strong transcription signals such as promoters and/or enhancers. However, it is also possible to enhance translation by, for example, improving the stability of the mRNA.

Suitable promoters in the expression cassette are in principle all promoters which are able to control the expression of foreign genes in organisms, advantageously in plants or fungi. It is preferable to use in particular plant promoters or promoters derived from a plant virus. Advantageous regulatory sequences for the novel process are present, for example, in promoters such as cos, tac, trp, tet, trp-tet, lpp, lac, lpp-lac, lacI$^q$, T7, T5, T3, gal, trc, ara, SP6, λ-P$_R$ or in the λ-P$_L$ promoter, which are advantageously used in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters such as CaMV/35S [Franck et al., Cell 21(1980) 285–294], SSU, OCS, lib4, STLS1, B33, nos (=nopaline synthase promoter) or in the ubiquitin promoter. The expression cassette may also comprises a chemically inducible promoter by which expression of the exogenous Δ6-ACETYLENASE/Δ6-DESATURASE and/or Δ6-DESATURASE gene in the organism, advantageously in the plants, can be controlled at a particular time. Examples of such advantageous plant promoters are the PRP1 promoter [Ward et al., Plant. Mol. Biol. 22(1993), 361–366], a benzenesulfonamide-inducible (EP 388186), a tetracycline-inducible (Gatz et al., (1992) Plant J. 2, 397–404), a salicylic acid-inducible promoter (WO 95/19443), an abscisic acid-inducible (EP335528) or an ethanol- or cyclohexanone-inducible (WO93/21334) promoter. Further examples of plant promoters which can advantageously be used are the promoter of the cytosolic FBPase from potato, the ST-LSI promoter from potato (Stockhaus et al., EMBO J. 8 (1989) 2445–245 [lacuna]), the promoter of phosphoribosyl-pyrophosphate amidotransferase from Glycine max (see also Genbank Accession Number U87999) or a node-specific promoter as in EP 249676. Particularly advantageous plant promoters are those which ensure expression in tissues or plant parts/organs in which fatty acid biosynthesis of its precursors takes place, such as, for example, in the endosperm or in the developing embryo. Particular mention should be made of advantageous promoters which ensure seed-specific expression, such as, for example, the USP promoter or derivatives thereof, the LEB4 promoter, the phaseolin promoter or the napin promoter. The particularly advantageous USP promoter or its derivatives mediate gene expression very early in seed development (Baeumlein et al., Mol Gen Genet, 1991, 225 (3): 459–67). Further advantageous seed-specific promoters which can be used for monocotyledonous and dicotyledonous plants are the promoters suitable for dicotyledons, such as the napin gene promoter from oilseed rape (U.S. Pat. No. 5,608,152), the oleosin promoter from arabidopsis (WO98/45461), the phaseolin promoter from *Phaseolus vulgaris* (U.S. Pat. No. 5,504, 200), the Bce4 promoter from brassica (WO91/13980) or the legume B4 promoter (LeB4, Baeumlein et al., Plant J., 2, 2, 1992: 233–239) or promoters suitable for monocotyledons, such as the promoters of the lpt2 or lpt1 gene from barley (WO95/15389 and WO95/23230) or the promoters of the barley hordein gene, of the rice glutelin gene, of the rice oryzin gene, of the rice prolamin gene, of the wheat gliadin gene, of the wheat glutelin gene, of the corn zein gene, of the oats glutelin gene, of the sorghum kasirin gene or of the rye secalin gene, which are described in WO99/16890.

Further particularly preferred promoters are those which ensure expression in tissues or plant parts in which, for example, the biosynthesis of fatty acids, oils and lipids or their precursors takes place. Particular mention should be made of promoters which ensure seed-specific expression. Mention should be made of the promoter of the napin gene from oilseed rape (U.S. Pat. No. 5,608,152), the USP promoter from Vicia faba (USP=unknown seed protein, Baeumlein et al., Mol Gen Genet, 1991, 225 (3): 459–67), of the oleosin gene from arabidopsis (WO98/45461), of the phaseolin promoter (U.S. Pat. No. 5,504,200) or of the promoter of the legumin B4 gene (LeB4; Baeumlein et al., 1992, Plant Journal, 2 (2): 233–9). Mention should further be made of promoters such as that of the lpt2 or lpt1 gene from barley (WO95/15389 and WO95/23230), which confers seed-specific expression in monocotyledonous plants.

The expression cassette (=gene construct, nucleic acid construct) may, as described above, comprise other genes which are to be introduced into the organisms. These genes may be under separate regulation or under the same regulatory region as the genes of Δ6-ACETYLENASE/Δ6-DESATURASE and/or Δ6-DESATURASE. Examples of these genes are further biosynthesis genes, advantageously of fatty acid biosynthesis, which make increased synthesis possible. Examples which may be mentioned are the genes for the Δ15-, Δ12-, Δ9-, Δ6-, and Δ5-desaturases, the various hydroxylases, the Δ12-acetylenase, the acyl ACP thioesterases, β-ketoacyl ACP synthases or β-ketoacyl ACP reductases. It is advantageous to use the desaturase genes in the nucleic acid construct.

It is possible in principle for all natural promoters with their regulatory sequences like those mentioned above to be used for the novel expression cassette and the novel process, as described below. It is also possible and advantageous moreover to use synthetic promoters.

For preparation of an expression cassette, it is possible to manipulate various DNA fragments in order to obtain a nucleotide sequence which expediently reads in the correct direction and which is equipped with a correct reading frame. To link the DNA fragments (=novel nucleic acids) together it is possible to attach adaptors or linkers to the fragments.

It is possible and expedient for the promoter and terminator regions to be provided in the direction of transcription with a linker or polylinker which contains one or more restriction sites for insertion of this sequence. The linker ordinarily has 1 to 10, usually 1 to 8, preferably 2 to 6, restriction sites. The size of the linker within the regulatory region is generally less than 100 bp, frequently less than 60 bp, but at least 5 bp. The promoter may be both native or homologous and foreign or heterologous in relation to the host organism, for example to the host plant. The expression cassette comprises in the 5'-3' direction of transcription the promoter, a DNA sequence which codes for a Δ6-acetylenase/Δ6-desaturase and/or Δ6-desaturase gene, and a region for transcription termination. Various termination regions can replace one another as desired.

A further possibility is to employ manipulations which provide appropriate restriction cleavage sites or delete excess DNA or restriction cleavage sites. When it is a question of insertions, deletions or substitutions such as, for example, transitions and transversions, it is possible to use in vitro mutagenesis, primer repair, restriction or ligation. It is possible with suitable manipulations such as, for example, restriction, chewing back or filling in overhangs for blunt ends to provide complementary ends of the fragments for the ligation.

Attachment of the specific ER retention signal SEKDEL may, inter alia, be important for advantageous high-level expression (Schouten, A. et al., Plant Mol. Biol. 30 (1996), 781–792), this tripling or quadrupling the average level of expression. It is also possible to employ other retention signals which occur naturally with plant and animal proteins which are localized in the ER for constructing the cassette.

Preferred polyadenylation signals are plant polyadenylation signals, preferably those essentially corresponding to T-DNA polyadenylation signals from *Agrobacterium tumefaciens*, in particular of gene 3 of the T-DNA (octopine synthase) of the Ti plasmid pTiACH5 (Gielen et al., EMBO J. 3 (1984), 835 ff) or corresponding functional equivalents.

An expression cassette is prepared by fusing a suitable promoter to a suitable Δ6-acetylenase/Δ6-desaturase and/or Δ6-desaturase DNA sequence and to a polyadenylation signal by conventional recombination and cloning techniques as described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

For preparation of an expression cassette, it is possible to manipulate various DNA fragments in order to obtain a nucleotide sequence which expediently reads in the correct direction and which is equipped with a correct reading frame. To link the DNA fragments together it is possible to attach adaptors or linkers to the fragments.

It is possible and expedient for the promoter and terminator regions to be provided in the direction of transcription with a linker or polylinker which contains one or more restriction sites for insertion of this sequence. The linker ordinarily has 1 to 10, usually 1 to 8, preferably 2 to 6, restriction sites. The size of the linker within the regulatory region is generally less than 100 bp, frequently less than 60 bp, but at least 5 bp. The promoter may be both native or homologous and foreign or heterologous in relation to the host plant. The expression cassette comprises in the 5'-3' direction of transcription the promoter, a DNA sequence which codes for a Δ6-acetylenase/desaturase gene, and a region for transcription termination. Various termination regions can replace one another as desired.

For preparation of an expression cassette, it is possible to manipulate various DNA fragments in order to obtain a nucleotide sequence which expediently reads in the correct direction and which is equipped with a correct reading frame. To link the DNA fragments together it is possible to attach adaptors or linkers to the fragments.

It is possible and expedient for the promoter and terminator regions to be provided in the direction of transcription with a linker or polylinker which contains one or more restriction sites for insertion of this sequence. The linker ordinarily has 1 to 10, usually 1 to 8, preferably 2 to 6, restriction sites. The size of the linker within the regulatory region is generally less than 100 bp, frequently less than 60 bp, but at least 5 bp. The promoter may be both native or homologous and foreign or heterologous in relation to the host plant. The expression cassette comprises in the 5'-3' direction of transcription the promoter, a DNA sequence which codes for a Δ6-acetylenase/Δ6-desaturase or Δ6-desaturase gene, and a region for transcription termination. Various termination regions can replace one another as desired.

The DNA sequence coding for a Δ6-acetylenase/Δ6-desaturase and/or Δ6-desaturase from *Ceratodon purpureus* comprises all the sequence features necessary to achieve a localization correct for the site of fatty acid, lipid or oil biosynthesis. Thus no other targeting sequences are necessary per se. However, such a localization may be desirable and advantageous and therefore be artificially modified or enhanced so that such fusion constructs are also a preferred and advantageous embodiment of the invention.

Particularly preferred sequences are those ensuring targeting in plastids. In certain circumstances, targeting in other components (reported: Kermode, Crit. Rev. Plant Sci. 15, 4 (1996), 285–423), for example in the vacuoles, in the mitochondrium, in the endoplasmic reticulum (ER), peroxisomes, lipid bodies or, through absence of appropriate operative sequences, remaining in the compartment of production, the cytosol, may also be desirable.

It is advantageous for the novel nucleic acid sequences to be cloned together with at least one reporter gene into an expression cassette which is introduced into the organism via a vector or directly into the genome. This reporter gene should make easy detection possible by a growth, fluorescence, chemo- or bioluminescence or resistance assay or by a photometric measurement. Examples of reporter genes which may be mentioned are antibiotic- or herbicide-resistance genes, hydrolase genes, fluorescent protein genes, bioluminescence genes, sugar or nucleotide metabolism genes or biosynthesis genes such as the Ura3 gene, the Ilv2 gene, the luciferase gene, the β-galactosidase gene, the gfp gene, the 2-deoxyglucose-6-phosphate phosphatase gene, the β-glucuronidase gene, β-lactamase gene, the neomycin phosphotransferase gene, the hygromycin phosphotransferase gene or the BASTA (=glufosinate-resistance) gene. These genes make it possible easily to measure and quantify the transcription activity and thus the expression of the genes. It is thus possible to identify sites in the genome which show differences in productivity.

In a preferred embodiment, an expression cassette comprises a promoter upstream, i.e. at the 5' end of the coding sequence, and a polyadenylation signal downstream, i.e. at the 3' end, and, where appropriate, further regulatory elements which are operatively linked to the coding sequence in between for the Δ6-acetylenase/Δ6-desaturase and/or Δ6-desaturase DNA sequence. Operative linkage means the sequential arrangement of promoter, coding sequence, terminator and, where appropriate, further regulatory elements in such a way that each of the regulatory elements can carry out its function as intended in the expression of the coding sequence. The sequences preferred for the operative linkage are targeting sequences to ensure subcellular localization in plastids. However, targeting sequences to ensure subcellular localization in the mitochondrium, in the endoplasmic reticulum (ER), in the cell nucleus, in elaioplasts or other compartments can also be employed if required, as well as translation enhancers such as the 5' leader sequence from tobacco mosaic virus (Gallie et al., Nucl. Acids Res. 15 (1987), 8693–8711).

An expression cassette may comprise, for example, a constitutive promoter (preferably the USP or napin promoter), the gene to be expressed and the ER retention signal. The ER retention signal preferably used is the amino acid sequence KDEL (lysine, aspartic acid, glutamic acid, leucine).

For expression, the expression cassette is inserted into a prokaryotic or eukaryotic host organism, for example a microorganism such as a fungus or a plant, advantageously into a vector such as, for example, a plasmid, a phage or other DNA, which enables the genes to be optimally expressed in the host organism. Examples of suitable plasmids are in *E. coli* pLG338, pACYC184, pBR series such as, for example, pBR322, pUC series such as pUC18 or pUC19, M113mp series, pKC30, pRep4, pHS1, pHS2, pPLc236, pMBL24, pLG200, pUR290, pIN-III$^{113}$-B1, λgt11 or pBdCI, in streptomyces pIJ101, pIJ364, pIJ702 or pIJ361, in bacillus pUB110, pC194 or pBD214, in corynebacterium pSA77 or pAJ667, in fungi pALS1, pIL2 or pBB116, further advantageous fungal vectors being described by Romanos, M. A. et al., [(1992) "Foreign gene expression in yeast: a review", *Yeast* 8: 423–488] and van den Hondel, C. A. M. J. J. et al. [(1991) "Heterologous gene expression in filamentous fungi] and in More Gene Manipulations in Fungi [J. W. Bennet & L. L. Lasure, eds., p. 396–428: Academic Press: San Diego] and in "Gene transfer systems and vector development for filamentous fungi" [van den Hondel, C. A. M. J. J. & Punt, P. J. (1991) in: Applied Molecular Genetics of Fungi, Peberdy, J. F. et al., eds., p. 1–28, Cambridge University Press: Cambridge]. Examples of advantageous yeast promoters are 2 μM, pAG-1, YEp6, YEp13 and pEMBLYe23. Examples of algal or plant promoters are pLGV23, pGHlac$^+$, pBIN19, pAK2004, pVKH and pDH51 (see Schmidt, R. and Willmitzer, L., 1988). The abovementioned vectors or derivatives of the aforementioned vectors represent a small selection of the possible plasmids. Further plasmids are well known to the skilled worker and can be found, for example, in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), Chapters 6/7, pp. 71–119. Advantageous vectors are shuttle vectors or binary vectors which replicate in *E. coli* and *Agrobacterium*.

Apart from plasmids, vectors also mean all other vectors known to the skilled worker, such as, for example, phages, viruses such as SV40, CMV, baculovirus, adenovirus, transposons, IS elements, phasmids, phagemids, cosmids, linear or circular DNA. These vectors are capable of autonomous replication or chromosomal replication in the host organism; chromosomal replication is preferred.

In a further embodiment of the vector, the novel expression cassette can also advantageously be introduced in the form of a linear DNA into the organisms and be integrated by heterologous or homologous recombination into the genome of the host organism. This linear DNA may consist of a linearized plasmid or only of the expression cassette as vector or the novel nucleic acid sequences.

In a further advantageous embodiment, the novel nucleic acid sequence can also be introduced alone into an organism.

If further genes, in addition to the novel nucleic acid sequence, are to be introduced into the organism, it is possible to introduce all together with a reporter gene in a single vector or each individual gene with a reporter gene in one vector in each case into the organism, in which case the various vectors can be introduced simultaneously or successively.

The vector advantageously comprises at least one copy of the novel nucleic acid sequences and/or of the novel expression cassette.

It is possible for example to incorporate the plant expression cassette into the tobacco transformation vector pBinAR. FIG. 1 shows the tobacco transformation vectors pBinAR with 35S promoter (C) and pBin-USP with the USP promoter (D). The initial vectors are depicted in FIG. 1 A) and B).

An alternative possibility is also in vitro transcription and translation of a recombinant vector (=expression vector), for example by using the T7 promoter and T7 RNA polymerase.

Expression vectors used in prokaryotes frequently make use of inducible systems with and without fusion proteins or fusion oligopeptides, it being possible for these fusions to take place both N-terminally and C-terminally or on other domains which can be used in a protein. Fusion vectors of this type are usually employed for: i.) increasing the RNA expression rate, ii.) increasing the protein synthesis rate which can be achieved, iii.) increasing the solubility of the protein, or iv.) simplifying the purification by a binding sequence which can be used for affinity chromatography. Proteolytic cleavage sites are frequently also introduced via fusion proteins, enabling elimination of a part of the fusion protein also of the purification. Such recognition sequences for proteases recognize, for example, factor Xa, thrombin and enterokinase.

Typical advantageous fusion and expression vectors are pGEX [Pharmacia Biotech Inc; Smith, D. B. and Johnson, K. S. (1988) *Gene* 67: 31–40], pMAL (New England Biolabs, Beverly, Mass.) and pRIT5 (Pharmacia, Piscataway, N.J.) which comprises glutathione S-transferase (GST), maltose binding protein, or protein A.

Further examples of *E. coli* expression vectors are pTrc [Amann et al., (1988) *Gene* 69:301–315] and pET vectors [Studier et al., Gene Expression Technology: Methods in Enzymology 185, Academic Press, San Diego, Calif. (1990) 60–89; Stratagene, Amsterdam, The Netherlands].

Further advantageous vectors for use in yeasts are pYepSec1 (Baldari, et al., (1987) *Embo J.* 6:229–234), pMFa (Kurjan and Herskowitz, (1982) *Cell* 30:933–934), pJRY88 (Schultz et al., (1987) *Gene* 54:113–123), and pYES derivatives (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi", in: Applied Molecular Genetics of Fungi, J. F. Peberdy, et al., eds., p. 1–28, Cambridge University Press: Cambridge.

An alternative and advantageous possibility is also to use insect cell expression vectors, e.g. for expression in Sf 9 cells. Examples thereof are the vectors of the pAc series (Smith et al. (1983) *Mol. Cell Biol.* 3:2156–2165) and of the pVL series (Lucklow and Summers (1989) *Virology* 170: 31–39).

It is additionally possible and advantageous to use plant cells or algal cells for the gene expression. Examples of plant expression vectors are to be found in Becker, D., et al. (1992) "New plant binary vectors with selectable markers located proximal to the left border", *Plant Mol. Biol.* 20: 1195–1197 or in Bevan, M. W. (1984) "Binary *Agrobacterium* vectors for plant transformation", *Nucl. Acid. Res.* 12: 8711–8721.

The novel nucleic acid sequences may also be expressed in mammalian cells. Examples of appropriate expression vectors are pCDM8 and pMT2PC, mentioned in: Seed, B. (1987) Nature 329:840 or Kaufman et al. (1987) EMBO J. 6: 187–195). In these cases, the promoters preferably used are of viral origin such as, for example, promoters of polyomavirus, adenovirus 2, cytomegalovirus or simian virus 40. Further prokaryotic and eukaryotic expression systems are mentioned in Chapters 16 and 17 in Sambrook et al., *Molecular Cloning: A Laboratory Manual*, 2nd, ed., Cold Spring Harbor Laboratory, Cold Spring Harbor Laboratory Press, Cold Spring Harbor, N.Y., 1989.

The introduction of the novel nucleic acids, of the expression cassette or of the vector into organisms, for example into plants, can in principle take place by all methods known to the skilled worker.

The skilled worker can find appropriate methods for microorganisms in the textbooks by Sambrook, J. et al. (1989) Molecular Cloning: A Laboratory Manual, Cold Spring Harbor Laboratory Press, by F. M. Ausubel et al. (1994) Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Harbor Laboratory Press or Guthrie et al., Guide to Yeast Genetics and Molecular Biology, Methods in Enzymology, 1994, Academic Press.

The transfer of foreign genes into the genome of a plant is referred to as transformation. In this case, the methods described for the transformation and regeneration of plants from plant tissues or plant cells for transient or stable transformation are utilized. Suitable methods are protoplast transformation by polyethylene glycol-induced DNA uptake, the biolistic method with the gene gun—the so-called particle bombardment method, electroporation, incubation of dry embryos in DNA-containing solution, microinjection and agrobacterium-mediated gene transfer. The methods mentioned are described, for example, in B. Jenes et al., Techniques for Gene Transfer, in: Transgenic Plants, Vol. 1, Engineering and Utilization, edited by S. D. Kung and R. Wu, Academic Press (1993) 128–143 and in Potrykus Annu. Rev. Plant Physiol. Plant Molec. Biol. 42 (1991) 205–225. The construct to be expressed is preferably cloned into a vector which is suitable for transforming *Agrobacterium tumefaciens*, for example pBin19 (Bevan et al., Nucl. Acids Res. 12 (1984) 8711). Agrobacteria transformed with such a vector can then be used in a known manner for transforming plants, in particular crop plants such as, for example, tobacco plants, by, for example, bathing wounded leaves or pieces of leaves in a solution of agrobacteria and then cultivating in suitable media. Transformation of plants with *Agrobacterium tumefaciens* is described, for example, by Höfgen and Willmitzer in Nucl. Acids Res. (1988) 16, 9877, or is disclosed inter alia in F. F. White, Vectors for Gene Transfer in Higher Plants; in Transgenic Plants, Vol. 1, Engineering and Utilization, edited by S. D. Kung and R. Wu, Academic Press, 1993, pp. 15–38.

Agrobacteria transformed with a novel expression vector can likewise be used in a known manner for transforming plants such as test plants such as arabidopsis or crop plants such as cereals, corn, oats, rye, barley, wheat, soybean, rice, cotton, sugarbeet, canola, sunflower, flax, hemp, potato, tobacco, tomato, carrot, paprika, oilseed rape, tapioca, manioc, arrowroot, tagetes, alfalfa, lettuce and the various tree, nut and vine species, in particular oil-bearing crop plants such as soybean, peanut, ricinus, sunflower, corn, cotton, flax, oilseed rape, coconut, oil palm, safflower (*Carthamus tinctorius*) or cocoa bean, e.g. by bathing wounded leaves or pieces of leaves in a solution of agrobacteria and then cultivating in suitable media.

The genetically modified plant cells can be regenerated by all methods known to the skilled worker. Appropriate methods can be found in the abovementioned publications by S. D. Kung and R. Wu, Potrykus or Höfgen and Willmitzer.

Organisms or host organisms suitable and advantageous in principle for the novel nucleic acid, the expression cassette or the vector are all organisms able to synthesize fatty acids, specifically unsaturated fatty acids, or suitable for expressing recombinant genes. Examples which may be mentioned are plants such as arabidopsis, asteraceae such as calendula or crop plants such as soybean, peanut, ricinus, sunflower, corn, cotton, flax, oilseed rape, coconut, oil palm, safflower (*Carthamus tinctorius*) or cocoa bean, microorganisms such as fungi, for example the genus *Mortierella*, *Saprolegnia* or *Pythium*, bacteria such as the genus *Escherichia*, yeasts such as the genus *Saccharomyces*, cyanobacteria, ciliates, algae or protozoa such as dinoflagellates such as crypthecodinium. Preference is given to organisms able naturally to synthesize oils in relatively large amounts, such as fungi such as *Mortierella alpina*, *Pythium insidiosum* or plants such as soybean, oilseed rape, coconut, oil palm, safflower, ricinus, calendula, peanut, cocoa bean or sunflower or yeasts such as *Saccharomyces cerevisiae*, and particular preference is given to soybean, oilseed rape, sunflower, calendula or *Saccharomyces cerevisiae*. Transgenic animals are also suitable in principle as host organisms, for example *C. elegans*.

Host cells which can be used are also mentioned in: Goeddel, *Gene Expression Technology: Methods in Enzymology* 185, Academic Press, San Diego, Calif. (1990).

Expression strains which can be used, for example those having a relatively low protease activity, are described in: Gottesman, S., *Gene Expression Technology: Methods in Enzymology* 185, Academic Press, San Diego, Calif. (1990) 119–128.

The invention further relates to the use of an expression cassette comprising DNA sequences coding for a Δ6-acetylenase/Δ6-desaturase and/or Δ6-desaturase gene or DNA sequences hybridizing with the latter for the transformation of plant cells or tissues or parts of plants. The use is aimed at increasing the content of fatty acids, oils or lipids with an increased content of triple bonds and double bond in position 6.

It is moreover possible, depending on the choice of the promoter, for expression of the Δ6-acetylenase/Δ6-desaturase and/or Δ6-desaturase gene to take place specifically in the leaves, in the seeds, the tubers or other parts of the plant. Transgenic plants overproducing such fatty acids, oils or lipids with Δ6 triple bonds or Δ6 double bonds, their propagation material, and their plant cells, tissues or parts are a further aspect of the present invention. The invention preferably relates to transgenic plants comprising a novel functional or nonfunctional (=antisense DNA or enzymatically inactive enzyme) nucleic acid sequence or a functional or nonfunctional expression cassette.

The expression cassette or the novel nucleic acid sequences comprising a Δ6-acetylenase/Δ6-desaturase and/or Δ6-desaturase gene sequence can moreover be used to transform the organisms mentioned above by way of example, such as bacteria, cyanobacteria, yeasts, filamentous fungi, ciliates and algae with the aim of increasing the content of fatty acids, oil or lipids with Δ6 triple bonds or Δ6 double bonds.

Increasing the content of fatty acids, oils or lipids with Δ6 triple bonds or Δ6 double bonds means for the purpose of the present invention for example the artificially acquired capability of increased biosynthetic activity through functional overexpression of the Δ6-acetylenase/Δ6-desaturase and/or Δ6-desaturase gene in the novel organisms, advantageously in the novel transgenic plants, compared with the initial plants without genetic modification, at least for the duration of at least one plant generation.

The site of biosynthesis of fatty acids, oils or lipids for example is generally the seed or cellular layers of the seed, so that seed-specific expression of the Δ6-acetylenase/Δ6-desaturase and/or Δ6-desaturase gene is sensible. However, it is obvious that biosynthesis of fatty acids, oils or lipids need not be restricted to the seed tissue but may also take place in a tissue-specific manner in all other parts of the plants—for example in epidermis cells or in the tubers.

In addition, constitutive expression of the exogenous Δ6-acetylenase/Δ6-desaturase and/or Δ6-desaturase gene is advantageous. However, on the other hand, inducible expression may also appear desirable.

The effectiveness of expression of the transgenic Δ6-acetylenase/Δ6-desaturase and/or Δ6-desaturase gene can be determined, for example, in vitro by shoot meristem propagation. In addition, an alteration in the nature and level of expression of the Δ6-acetylenase/Δ6-desaturase and/or Δ6-desaturase gene and its effect on fatty acid, oil or lipid biosynthetic activity can be tested in glasshouse experiments on test plants.

The invention additionally relates to transgenic plants transformed with an expression cassette comprising a Δ6-acetylenase/Δ6-desaturase and/or Δ6-desaturase gene sequence or DNA sequences hybridizing with the latter, and to transgenic cells, tissues, parts and propagation material of such plants. Particularly preferred in this connection are transgenic crop plants such as, for example, barley, wheat, rye, oats, corn, soybean, rice, cotton, sugarbeet, oilseed rape and canola, sunflower, flax, hemp, potato, tobacco, tomato, tapioca, manioc, arrowroot, alfalfa, lettuce and the various tree, nut and vine species.

Plants for the purpose of the invention are mono- and dicotyledonous plants or algae.

Another novel embodiment comprises the transgenic plants which are described above and which comprise a functional or nonfunctional novel nucleic acid sequence or a functional or nonfunctional novel expression cassette. Nonfunctional means that there is no longer synthesis of an enzymatically active protein. In addition, nonfunctional nucleic acids or nucleic acid constructs also mean a so-called antisense DNA which results in transgenic plants which show a reduction in the enzymatic activity or no enzymatic activity. The antisense technique can be used, especially when the novel nucleic acid sequence is combined with other fatty acid synthesis genes in the antisense DNA, to synthesize triglycerides with an increased content of saturated fatty acids or to synthesize saturated fatty acids. Transgenic plants mean individual plant cells and their cultures on solid media or in liquid culture, parts of plants and whole plants.

The invention further relates to:

A process for transforming a plant, which comprises introducing expression cassettes comprising a Δ6-acetylenase/Δ6-desaturase and/or Δ6-desaturase gene sequence or DNA sequences hybridizing with the latter into a plant cell, into callus tissue, a whole plant or protoplasts of plants.

The use of Δ6-acetylenase/Δ6-desaturase and/or Δ6-desaturase DNA gene sequence or DNA sequences hybridizing with the latter for producing plants with an increased content of fatty acids, oils or lipids with triple bonds or delta-6 double bonds by expressing this Δ6-acetylenase/desaturase DNA in plants.

A protein comprising the amino acid sequence depicted in SEQ ID NO: 8.

A protein comprising the amino acid sequence depicted in SEQ ID NO: 10.

The use of the proteins having the sequences SEQ ID NO: 8 and SEQ ID NO: 10 for producing unsaturated fatty acids.

The invention further relates to a process for producing unsaturated fatty acids, which comprises introducing at least one novel nucleic acid sequence described above or at least one novel nucleic acid construct into a preferably oil-producing organism, culturing this organism and isolating the oil contained in the organism, and liberating the fatty acids contained in the oil. These unsaturated fatty acids advantageously contain Δ6 triple and/or Δ6 double bonds. The fatty acids can also be liberated from the oils or lipids for example by basic hydrolysis, for example with NaOH or KOH.

The invention additionally relates to a process for preparing triglycerides with an increased content of unsaturated fatty acids, which comprises introducing at least one novel nucleic acid sequence described above or at least one novel expression cassette into an oil-producing organism, culturing this organism, and isolating the oil contained in the organism.

The invention further relates to a process for the preparation of triglycerides with an increased content of unsaturated fatty acids by incubating triglycerides with saturated or unsaturated or saturated and unsaturated fatty acids with at least one of the proteins encoded by one of the sequences SEQ ID NO: 1, SEQ ID NO: 3, SEQ ID NO: 8, SEQ ID NO: 10 or SEQ ID NO: 11. The process is advantageously carried out in the presence of compounds able to take up or release reducing equivalents. The fatty acids can then be liberated from the triglycerides.

A process as claimed in claim 16 or 17, wherein the fatty acids are liberated from the triglycerides.

The abovementioned processes advantageously make it possible to synthesize fatty acids or triglycerides with an increased content of fatty acids with Δ6 triple and/or Δ6 double bonds.

The so-called antisense technology can be used in a process also to prepare fatty acids or triglycerides with an increased content of saturated fatty acids.

Examples of organisms which may be mentioned for said processes are plants such as arabidopsis, barley, wheat, rye, oats, corn, soybean, rice, cotton, sugarbeet, oilseed rape and canola, sunflower, flax, hemp, potato, tobacco, tomato, tapioca, manioc, arrowroot, alfalfa, peanut, ricinus, coconut, oil palm, safflower (*Carthamus tinctorius*) or cocoa bean, microorganisms such as the fungi *Mortierella, Saprolegnia* or *Pythium,* bacteria such as the genus *Escherichia,* cyanobacteria, yeasts such as the genus *Saccharomyces,* algae or protozoa such as dinoflagellates such as crypthecodinium. Organisms able naturally to synthesize oils in relatively large amounts are preferred, such as microorganisms such as fungi such as *Mortierella alpina, Pythium insidiosum* or plants such as soybean, oilseed rape, coconut, oil palm, safflower, ricinus, calendula, peanut, cocoa bean or sunflower or yeasts such as *Saccharomyces cerevisiae;* particular preference is given to soybean, oilseed rape, sunflower, carthamus or *Saccharomyces cerevisiae.*

The organisms used in the processes are grown or cultured in a manner known to the skilled worker, depending on the host organism. Microorganisms are ordinarily cultured in a liquid medium which contains a source of carbon, usually in the form of sugars, a source of nitrogen, usually in the form of organic sources of nitrogen, such as yeast extract or salts such as ammonium sulfate, trace elements such as iron, manganese, magnesium salts and, where appropriate, vitamins, at temperatures between 0° C. and 100° C., preferably between 10° C. and 60° C., while passing in oxygen. The pH of the nutrient liquid can be kept at a fixed value during this, that is to say controlled during the cultivation, or not. The cultivation can be carried out batchwise, semibatchwise or continuously. Nutrients can be introduced at the start of the fermentation or be subsequently fed in semicontinuously or continuously.

After transformation, plants are initially regenerated as described above and then cultured or grown in a usual way.

After cultivation, the lipids are isolated from the organisms in the usual way. For this purpose, the organisms can after harvesting be initially disrupted or used directly. The lipids are advantageously extracted with suitable solvents such as apolar solvents such as hexane or ethanol, isopropanol or mixtures such as hexane/isopropanol, phenol/chloroform/isoamyl alcohol at temperatures between 0° C. and 80° C., preferably between 20° C. and 50° C. The biomass is ordinarily extracted with an excess of solvent, for example a 1:4 excess of solvent relative to biomass. The solvent is subsequently removed, for example by distillation. The extraction can also take place with supercritical $CO_2$. The biomass remaining after the extraction can be removed, for example, by filtration.

The crude oil obtained in this way can then be further purified, for example by removing turbidity by adding polar solvents such as acetone or chloroform and subsequently filtering or centrifuging. Further purification on columns is also possible.

To isolate the free fatty acids from the triglycerides, the latter are hydrolyzed in a usual way.

The invention further relates to unsaturated fatty acids and triglycerides with an increased content of unsaturated fatty acids which have been prepared by the abovementioned processes, and to the use thereof for producing human foods, animal feed, cosmetics or pharmaceuticals. For these purposes, they are added to the human foods, the animal feed, the cosmetics or pharmaceuticals in conventional amounts.

The invention is explained in detail by the following examples:

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, cultivation of bacteria and recombinant DNA sequence analysis were carried out as described by Sambrook et al. (1989) (Cold Spring Harbor Laboratory Press: ISBN 0-87969-309-6).

Example 2

Recombinant DNA Sequence Analysis

Recombinant DNA molecules were sequenced using an ABI laser fluorescence DNA sequencer by the method of Sanger (Sanger et al. (1977) Proc. Natl. Acad. Sci. USA 74, 5463–5467). Fragments resulting from a polymerase chain reaction were sequenced and checked to avoid polymerase errors in constructs to be expressed.

Example 3

Generation of Transgenic Oilseed Rape Plants (Modified Method of Moloney et al., 1992, Plant Cell Reports, 8:238–242)

Transgenic oilseed rape plants were generated using binary vectors in *Agrobacterium tumefaciens* C58C1: pGV2260 or *Escherichia coli* (Deblaere et al., 1984, Nucl. Acids. Res. 13, 4777–4788). Oilseed rape plants (Var. Drakkar, NPZ Nordeutsche Pflanzenzucht, Hohenlieth, Germany) were transformed by using a 1:50 dilution of an overnight culture of a positively transformed agrobacteria colony in Murashige-Skoog medium (Murashige and Skoog 1962 Physiol. Plant. 15, 473) with 3% sucrose (3MS medium). Petioles or hypocotyledons from freshly germinated sterile oilseed rape plants (about 1 $cm^2$ each) were incubated with a 1:50 dilution of agrobacteria in a Petri dish for 5–10 minutes. This was followed by incubation on 3MS medium with 0.8% Bacto agar at 25° C. in the dark for 3 days. After 3 days, cultivation was continued with 16 hours of light/8 hours of dark and, in a weekly rhythm, continued on MS medium with 500 mg/l Claforan (cefotaxime sodium), 50 mg/l kanamycin, 20 microM benzylaminopurine (BAP) and 1.6 g/l glucose. Growing shoots were transferred to MS medium with 2% sucrose, 250 mg/l Claforan and 0.8% Bacto agar. If no roots formed after three weeks, the growth hormone 2-indolebutyric acid was added to the medium for rooting.

Example 4

Generation of Transgenic *Arabidopsis thaliana* Plants

*Arabidopsis thaliana* var. Columbia Col 0 (Lehle Seeds, Round Rock, Tex., USA) was transformed by the flower infiltration method described by: Bechtold, N., Ellis, J. and Pelletier, G. in Planta, *Agrobacterium* mediated gene transfer by infiltration of adult *Arabidopsis thaliana* plants, C. R. Acad. Sci. Paris, Life Sciences 316 (1993), 1194–119 [lacuna] or by the root transformation method.

Example 5

Corn plants were transformed as described by Pareddy, D., Petolino, J., Skokut, T., Hopkins, N., Miller, M., Welter, M., Smith, K., Clayton, D., Pescitelli, S., Gould, A., Maize Transformation via Helium Blasting. Maydica. 42(2): 143–154, 1997.

Example 6

Isolation and Cloning of Δ6-acetylenase/Δ6-desaturase and Δ6-desaturase from *Ceratodon purpureus*

In order to isolate DNA sequences from *Ceratodon purpureus* which encode a Δ6-acetylenase/Δ6-desaturase and a $Δ^6$-desaturase, various degenerate oligonucleotide primers were derived from DNA sequences which encode Δ5-

(EMBL Accession No. Z81122) and Δ6-fatty acid desaturases (U79010, AJ222980, AF031477):

Primer A: 5' - TGG TGG AA(A/G) TGG A(A/C)I CA(C/T) AA - 3' (SEQ ID NO:13) forward primer, deduced from the amino acid sequence WWKW (N/T/K) H(N/K)

Primer B: 5' - (T/G)GI TGG AA(A/G) (T/G) (G/A)I (A/C)AI CA(C/T) AA - 3" (SEQ ID NO:14) forward primer, deduced from the amino acid sequence (G/W) WK (E/D/W) (N/Q/K)H(N/K)

Primer C: 5' -AT (A/T/G/C)T(T/G) (A/T/G/C)GG (A/G)AA (A/T/G/C)A(A/G) (A/G)TG (A/G)TG - 3' (SEQ ID NO: 15), reverse primer, deduced from the amino acid sequence (I/M) (H/Q/N) PF (L/F) HH By means of polymerase chain reaction (PCR) with single-stranded *C. purpureus* cDNA, two DNA fragments 557 bp (Cer3) and 575 bp (Cer16) in length were amplified with primer A and primer C, and one DNA fragment 560 bp (Cer1) in length was amplified with primer B and primer C. The following program was used for the amplification: 10 minutes at 94° C., pause for hot start at 72° C., followed by 32 cycles of 20 s at 94° C., 1 minute at 45° C. (annealing temperature, $T_m$) and 1 minute at 72° C., 1 cycle of 10 minutes at 72° C. and stop at 4° C. The taq-DNA polymerase (Gibco BRL) was used for the amplification.

The abovementioned double-stranded DNA fragments from the two PCR amplifications were ligated into the pGEM-T vector (Promega), transformed into *E. coli* XL1blue MRF' Kan (Stratagene) and sequenced using the ABI PRISM Big Dye Terminator Cycle Sequencing Ready Reaction Kit (Perkin-Elmer, Weiterstadt). The Cer1 and Cer3 DNA subsequences showed 70% identity. The abovementioned DNA subsequences encoded open reading frames of 173 amino acids in the case of Cer1 (SEQ ID NO: 5=Partial nucleotide sequence of Cer1 without primer and SEQ ID NO: 6=Partial deduced amino acid sequence of Cer1), 172 amino acids in the case of Cer3 (SEQ ID NO: 7=Partial nucleotide sequence of Cer3 without primer and SEQ ID NO: 8=Partial deduced amino acid sequence of Cer3) and 178 amino acids in the case of Cer16 (SEQ ID NO: 9=Partial nucleotide sequence of Cer16 without primer and SEQ ID NO: 10=Partial deduced amino acid sequence of Cer16) without primers. The derived protein sequence of Cer1 showed an amino acid identity to Cer3 of 64% and to Cer16 of 28%; Cer3 and Cer16, in turn, had an amino acid identity of 27%.

The Cer1 and Cer3 proteins show the greatest similarity with the *Physcomitrella patens* Δ6-acyl-lipid desaturase (Girke et al., Plant J., 15, 1998: 39–48), while Cer16 shows the greatest similarity to the Δ6-acyl-lipid desaturase and the Δ8-sphingolipid desaturase from higher plants.

A directed *Ceratodon purpureus* λZAP cDNA library was provided by Fritz Thummler, Department of Botany, University of Munich (Pasentsis et al., Plant J., 13, 1, 1998: 51–61). This *Ceratodon* library was subjected to a PCR test, in which specific primers were derived from the abovementioned DNA subsequences Cer1, Cer3 and Cer 16:

Specific forward and reverse primers:

Cer1: 5'-CGAATGAGTGCGACGAAC-3' (SEQ ID NO: 16)+5'-AATAACCTGGGCTCTCAC-3' (SEQ ID NO: 17)

Cer3: 5'-ATGAGGATATTGATACTCTC-3' (SEQ ID NO: 18)+5'-GCAATCTGGGCATTCACG-3' (SEQ ID NO: 19)

Cer16: 5'-GACATCAAAGCTCTTCTC-3' (SEQ ID NO: 20)+5'-GGCGATGAGAAGTGGTTC-3' (SEQ ID NO: 21)

A restriction analysis (HindIII and EcoRV) of the products amplified from the cDNA library by means of PCR showed the same restriction pattern in all three cases as that of the PCR amplificates from the ss-cDNA, i.e. the *Ceratodon* cDNA library contains the three clones Cer1, Cer3 and Cer16.

Example 7 cDNA Library Screening and Sequencing of the Full-length Clones

DNA minipreps in pGEM-T of the three ~570 bp PCR fragments Cer1, Cer3, Cer16 amplified from ss-cDNA (see Example 6) were handed over to M. Lee and S. Stymne to subject the full-length clones from a *Ceratodon purpureus* λZAP cDNA library to further screening. As yet, this cDNA library screening has provided two full-length clones of Cer1 and Cer3 with inserts of approx. 2.2 kb, which were subcloned as EcoRI/KpnI fragments from the λZAP vector into the EcoRI/KpnI cleavage sites of the puc19 vector (New England Biolabs) and transformed into *E. coli* JM105. Further screening of the cDNA library with Cer1 and Cer3 as low-stringency hybridization probes revealed that at least one further clone with Cer1 homology exists which might conceivably encode the $\Delta^5$-desaturase.

Two *E. coli* clones, Cer1-50 and Cer3-50, were sequenced completely. Cer1-50 has a length of 2003 bp (SEQ ID NO: 1=nucleotide sequence of the Δ6-acetylenase/Δ6-desaturase from *Ceratodon purpureus* with 5' and 3' untranslated regions and polyA) and encodes an open reading frame of 483 amino acids (SEQ ID NO: 2=deduced amino acid sequence of the Δ6-acetylenase/Δ6-desaturase from *Ceratodon purpureus*). Cer3-50 has a length of 2142 bp (SEQ ID NO: 11 nucleotide sequence [2142 bp] of the Δ6-desaturase from *Ceratodon purpureus* with 5' and 3' untranslated regions) with an open reading frame of 520 amino acids (SEQ ID NO: 12=deduced amino acid sequence of the Δ6-desaturase from *Ceratodon purpureus*). Both protein sequences show the highly-conserved HPGG motif from cytochrome $b_5$ at the N terminus (Lederer F., Biochimie 76, 1994: 674–692) and the three histidine boxes which are characteristic of desaturases at the C terminus (Shanklin et al., Biochemistry, 33, 1994: 12787–12794). Thus they constitute further members of the growing family of the cytochrome $b_5$ fusion proteins (Napier et al., Trends in Plant Science, 4, 1, 1999: 2–4). The first histidine of the third box is exchanged for glutamine, another characteristic of Δ5- and Δ6-acyl-lipid desaturases and Δ8-sphingolipid desaturases.

Example 8

Cloning of the complete functional active Δ6-acetylenase/Δ6-desaturase and Δ6-desaturase sequence by PCR and provision of this sequence for cloning into vectors, and functional expression in yeast.

A cDNA which codes for enzymes with Δ6-acetylenase/Δ6-desaturase activity from *Ceratodon purpureus* was prepared. The Δ6-desaturase was cloned in analogy to the example described herein (see SEQ ID NO: 2, SEQ ID NO: 4 and SEQ ID NO: 12).

This is done by initially deriving the oligonucleotides for a polymerase chain reaction (PCR) on the basis of the Cer1 cDNA for the Δ6-acetylenase/desaturase from *Ceratodon purpureus*.

Cer1: 5' - CC <u>GGTACC</u> ATG GCC CTC GTT ACC GAC - 3' (SEQ ID NO: 22)+5' - CC <u>GAATTC</u> TTA GTG AGC GTG AAG CCG - 3' (SEQ ID NO: 23)

Cer3: 5' - CC <u>GGTACC</u> ATG GTG TCC CAG GGC GGC - 3' (SEQ ID NO: 24)+5' - CC <u>GAATTC</u> TCA ACT CGC AGC AAG CTG - 3' (SEQ ID NO: 25)

The following primers derived from Cer 1 were adapted for expression in yeast:
5' primer: 5' -AAAAGGATCCAAAATGGCCCTCGTTAC- CGAC - 3' (SEQ ID NO: 26)
3' primer: 5' -AAAAGTCGACTTAGTGAGCGTGAA GCC - 3' (SEQ ID NO: 27)

A Δ6-acetylenase/desaturase cDNA from *Ceratodon purpureus* is used as template in a PCR. A BamHI restriction cleavage site is introduced with the aid of the primer in front of the start codon of the Δ6-acetylenase/desaturase cDNA. For directed cloning, a SalI restriction cleavage site is introduced behind the stop codon. The reaction mixtures contained about 1 ng/microl template DNA, 0.5 microM oligonucleotides and 200 microM deoxynucleotides (Pharmacia), 50 mM KCl, 10 mM Tris-HCl (pH 8.3 at 25° C., 1.5 mM $MgCl_2$) and 0.02 U/microl Pwo polymerase (Boehringer Mannheim) and are incubated in a Perkin Elmer PCR machine with the following temperature program:
Annealing temperature: 50° C., 52 sec
Denaturation temperature: 95° C., 52 sec
Elongation temperature: 72° C., 90 sec
Number of cycles: 30

The resulting fragment of 1467 base pairs is ligated into the vector pBluescript SK- (Stratagene) which has been cleaved with EcoRV. A clone is identified by control cleavage pBS-Cer1, whose insert can be excised in full length by BamHI/SalI (1452 base pairs plus 15 nucleotides of restriction cleavage sites) and has the following sequence (the start and stop codon is underlined, the cleavage sites are shown in italics). It is also possible analogously to use a cDNA sequence of the clone Cer50. This is a monofunctional delta-6-desaturase (see SEQ ID NO: 3). The derived amino acid sequence is to be found in SEQ ID NO: 4.

To check the functionality of the encoded enzyme in a microorganism, the 1467 bp BamHI/SalI fragment from pBS-Cer1 is ligated into the expression vector pYES2 (Invitrogen, Groningen, The Netherlands) which has been cut with BamHI/XhoI, and yeast is transformed by standard protocols with the newly produced plasmid pYES2-Cer1 (see Invitrogen transformation protocol, Groningen, The Netherlands). Resulting colonies are cultured on raffinose-containing medium, and Δ6-acetylenase/desaturase gene expression is induced with galactose (see below).

Example 9

Lipid Analysis of Transformed Yeasts

Yeasts are capable of incorporating not only endogenous fatty acids (16:0, 16:1, 18:0 and 18:1) but also exogenous fatty acids into their membrane lipids. To test the substrate specificity of the particular desaturase expressed, the CM-2% raffinose medium is supplemented before the inoculation with 1% Tergitol NP-40 (w/v, Sigma) to solubilize exogenous fatty acids and 0.003% of the fatty acid in question (stock solution: 0.3% or 3% fatty acid in 5% Tergitol NP-40, w/v). The preculture was carried out by inoculating 3 ml CM-2% raffinose medium/1% Tergitol NP-40 with a transgenic yeast colony and subsequently incubating the culture in a rolling apparatus for 2 days at 30° C. to an optical density at 600 nm ($OD_{600}$) of 4.0 to 4.3. For the main culture, 10 ml of CM-2% raffinose/1% Tergitol NP-40 medium ±0.003% fatty acid are inoculated with an aliquot of the preculture (200-fold dilution) to an $OD_{600}$ of 0.02 and incubated for 24 hours at 30° C., 250 rpm, in a shaker. The test cultures were induced during the logarithmic growth phase ($OD_{600}$ 0.5 to 0.6) by adding galactose to 1.8%. After the induced cells had been grown aerobically for a further 24 hours at 30° C., they were harvested at an $OD_{600}$ of 4.0 to 4.3.

The induced yeast cells are harvested by centrifugation for 10 minutes at 2000 g, resuspended in 3 ml of distilled water, boiled for 10 minutes at 100° C. and, after cooling on ice, resedimented. The cell sediment is hydrolyzed for 1 hour at 90° C. using 1 N methanolic sulfuric acid and 2% dimethoxypropane, and the lipids were transmethylated. The resulting fatty acid methyl esters (FAMEs) are extracted with petroleum ether. The extracted FAMEs are analyzed by gas liquid chromatography using a capillary column (Chrompack, WCOT Fused Silica, CP-Wax-52 CB, 25 m, 0.32 mm) and a temperature gradient of 170° C. to 240° C. in 20 minutes and 5 minutes at 240° C. The identity of the monoenoic, dienoic, trienoic and tetraenoic acid methyl esters is confirmed by comparison with suitable FAME standards (Sigma). No reference substances are available for the triynoic and tetraynoic acids. Their identity and the position of the triple bond are analyzed by means of GC-MS by subjecting the FAME mixtures to a suitable chemical derivatization, for example to give 4,4-dimethoxyoxazolin derivatives (Christie, 1998). The GC analyses of the fatty acid methyl esters from the transgenic yeasts which are transformed with the blank vector pYES2, with pYES2-Cer1 ($Δ^6$-acetylenase) is shown in Table 1. The transgenic yeast cells are analyzed without exogenous fatty acids or after addition of linoleic acid (18:2), γ-linolenic acid (γ-18:3), α-linolenic acid (α-18:3) or ω3-octadecatetraenoic acid (18:4).

Table 1 shows the GC analyses of the fatty acid methyl esters from transgenic yeasts which had been transformed with the blank vector pYES2, the Δ6-acetylenase (Cer1/pYES2) and the Δ6-desaturase (Cer3/pYES2). The transgenic yeast cells were analyzed without exogenous fatty acids (–) or after addition of linoleic acid (18:2), γ-linolenic acid (γ-18:3), α-linolenic acid (α-18:3) or ω3-octadecatetraenoic acid (18:4). Fatty acid composition in [mol %] of the total fatty acids, the incorporation of the fed fatty acids (bold, in black), the desaturation products (in red) and the total of the desaturation products (last line) of the individual feeding experiments being indicated.

Example 10

Generation of Transgenic Plants which Overexpress an Enzyme with Δ6-acetylenase/desaturase Activity To transform plants, a transformation vector which ligates the BamHI/SalI fragment from pBS-Cer1 into the vector pBin-USP which has been cleaved with BamHI/SalI or into pBinAR is generated. pBin-USP and pBinAR are derivatives of the plasmid pBin19. pBinAR was produced from pBin19, by inserting a 35S CaMV promoter as EcoRI-KpnI fragment (corresponding to nucleotides 6909–7437 of cauliflower mosaic virus) (Franck et al. (1980) Cell 21, 285) into pBin19 (Bevan et al. (1980) Nucl. Acids Res. 12, 8711). The polyadenylation signal of gene 3 of the T-DNA of the Ti plasmid pTiACH5 (Gielen et al., (1984) EMBO J. 3, 835), nucleotides 11749–11939, is isolated as PvuII-HindIII fragment and, after addition of SphI linkers to the PvuII cleavage site, cloned between the SphI-HindIII cleavage site of the vector. This resulted in the plasmid pBinAR (Höfgen and Willmitzer (1990) Plant Science 66, 221–230), there being, due to recloning from pBluescript, several restriction cleavage sites available between promoter and terminator. The USP promoter corresponds to nucleotides 1–684 (Genbank Accession X56240), with part of the noncoding region of the USP gene being present in the promoter. The promoter fragment which is 684 base pairs in size was amplified by a PCR by standard methods using commercially available T7 standard primers (Stratagene) and with the aid of a synthesized primer. (Primer sequence: 5'-GTCGACCCGCGGAC-TAGTGGGCCCTCTAGACCCGGGGATC-CGGATCTGCTGGCTATGAA - 3') (SEQ ID NO: 28).

The construct is employed for transforming *Arabidopsis thaliana* and oilseed rape plants.

Regenerated shoots are obtained on 2MS medium with kanamycin and Claforan and, after rooting, transferred into soil and, after cultivation for two weeks in an air-conditioned chamber or in a glasshouse, induced to flower, and ripe seeds are harvested and investigated for Δ6-acetylenase/desaturase expression by lipid analyses. Lines with increased contents of acetylenic fatty acids or double bonds at the delta-6 position are identified. An increased content of acetylenic fatty acids and double bonds at the delta-6 position compared with untransformed control plants is found in the stably transformed transgenic lines which functionally express the transgene.

Example 11

Lipid Extraction from Seeds

The analysis of lipids from plant seeds takes place in analogy to the analysis of yeast lipids. However, plant material is first homogenized mechanically using mortars in order to make it available for extraction.

TABLE 1

| Fatty acids | pYES2 | | | | | Cer1/pYES2 | | | | | Cer3/pYES2 | | | | |
|---|---|---|---|---|---|---|---|---|---|---|---|---|---|---|---|
| [mol %] | — | 18:2 | γ-18:3 | α-18:3 | 18:4 | — | 18:2 | γ-18:3 | α-18:3 | 18:4 | — | 18:2 | γ-18:3 | α-18:3 | 18:4 |
| 16:0 | 26.2 | 24.1 | 27.8 | 27.4 | 32.7 | 24.2 | 23.1 | 26.2 | 25.7 | 26.5 | 26.5 | 23.3 | 28.1 | 29.2 | 29.6 |
| $16:1^9$ | 41.8 | 9.6 | 27.4 | 27.3 | 16.1 | 36.5 | 13.3 | 24.7 | 28.8 | 21.9 | 43.8 | 9.9 | 25.2 | 34.0 | 20.9 |
| $16:2^{6,9}$ | | | | | | 6.9 | 1.8 | 3.3 | 5.3 | 3.0 | 1.1 | | 0.1 | 0.8 | 0.1 |
| 18:0 | 6.5 | 5.3 | 6.1 | 6.1 | 7.9 | 6.4 | 6.1 | 6.6 | 6.5 | 7.1 | 5.5 | 5.3 | 6.3 | 5.8 | 5.9 |
| $18:1^9$ | 23.6 | 4.9 | 15.1 | 14.8 | 11.3 | 24.9 | 8.8 | 15.6 | 20.0 | 16.8 | 21.4 | 5.3 | 15.7 | 14.3 | 11.5 |
| $18:2^{6,9}$ | | | | | | 0.3 | | 0.2 | 0.3 | 0.2 | 0.1 | | | 0.1 | |
| $18:2^{9,12}$ | | 53.9 | | | | | 41.9 | | | | | 42.3 | | | |
| $18:3^{6,9,12}$ | | | 19.5 | | | | 0.8 | 16.1 | | | | | 8.1 | 21.2 | |
| $18:3^{9,12,15}$ | | | | 22.8 | | | | | 10.0 | | | | | 11.9 | |
| $18:4^{6,9,12,15}$ | | | | | 28.8 | | | | 1.7 | 21.3 | | | | 1.9 | 30.1 |
| $18:3^{6yn,9,12}$ | | | | | | | 1.3 | 4.6 | | | | | | | |
| $18:4^{6yn,9,12,15}$ | | | | | | | | | | 2.3 | | | | | |
| Σ Des. [mol %] | — | — | — | — | — | 7.2 | 3.9 | 8.1 | 7.3 | 5.5 | 1.2 | 8.1 | 0.1 | 2.8 | 0.1 |

We claim:

1. An isolated nucleic acid sequence which codes for a polypeptide having Δ6-acetylenase and/or Δ6-desaturase activity, selected from the group consisting of:
   a nucleic acid sequence having the sequence depicted in SEQ ID NO: 1, SEQ ID NO: 3 or SEQ ID NO: 11,
   nucleic acid sequences which, as a result of the degeneracy of the genetic code, are derived from the nucleic acid sequence depicted in SEQ ID NO: 1, SEQ ID NO: 3 or SEQ ID NO: 11, and
   derivatives of the nucleic acid sequence depicted in SEQ ID NO: 1, SEQ ID NO: 3 or SEQ ID NO: 11, which encode polypeptides having the amino acid sequence depicted in SEQ ID NO: 2, or for a polypeptide having at least 95% homology thereof at the amino acid level and having at least 10% of the enzymatic action of the polypeptide containing the amino acid sequence in SEQ ID NO: 2.

2. An expression cassette comprising a nucleic acid sequence as claimed in claim 1, where the nucleic acid sequence is linked to one or more regulatory signals.

3. A vector comprising
   a nucleic acid sequence as claimed in claim 1, or
   an expression cassette comprising a nucleic acid sequence as claimed in claim 1, where the nucleic acid sequence is linked to one or more regulatory signals.

4. A transgenic plant comprising
   an expression cassette comprising a nucleic acid sequence as claimed in claim 1, wherein the nucleic acid sequence is linked to one or more regulatory signals.

5. A process for preparing unsaturated fatty acids, which comprises introducing at least one nucleic acid sequence as claimed in claim 1 or at least one expression cassette comprising a nucleic acid sequence as claimed in claim 1, where the nucleic acid sequence is linked to one or more regulatory signals into an oil-producing organism, culturing this organism and isolating the oil contained in the organism, and liberating the fatty acids contained in the oil.

6. A process for preparing triglycerides with an increased content of unsaturated fatty acids, which comprises introducing
   at least one nucleic acid sequence as claimed in claim 1 or
   at least one expression cassette comprising a nucleic acid sequence as claimed in claim 1, where the nucleic acid sequence is linked to one or more regulatory signals into an oil-producing organism, culturing this organism and isolating the oil contained in the organism.

7. A process as claimed in claim 5, wherein the unsaturated fatty acids have an increased content of unsaturated fatty acids with a triple bond or with a double bond in position 6 or a triple bond and a double bond in position 6.

8. A process as claimed in claim 5, wherein the organism is a plant or a microorganism.

9. A non-human organism comprising the isolated nucleic acid sequence as claimed in claim 1, wherein said organism is at least one of a plant and a microorganism.

10. A non-human organism comprising at least one expression cassette as claimed in claim 2, wherein said organism is at one of a plant and a microorganism.

11. A non-human organism comprising at least one vector as claimed in claim 2, wherein said organism is at one of a plant and a microorganism.

12. A non-human transgenic organism as claimed in claim 9, wherein the organism is a plant or, a microorganism.

13. A non-human transgenic organism as claimed in claim 10, wherein the organism is a plant or, a microorganism.

14. A non-human transgenic organism as claimed in claim 11, wherein the organism is a plant or, a microorganism.

* * * * *

UNITED STATES PATENT AND TRADEMARK OFFICE
CERTIFICATE OF CORRECTION

PATENT NO. : 7,183,458 B1  Page 1 of 1
APPLICATION NO. : 09/980468
DATED : February 27, 2007
INVENTOR(S) : Heinz et al.

It is certified that error appears in the above-identified patent and that said Letters Patent is hereby corrected as shown below:

In Claim 10, column 54, line 51 recites "is at one of plant and a microorganism" which should be corrected to recite --is at least one of a plant and microorganism--.

In Claim 11, column 54, lines 53-54 recites "is at one of plant and a micoorganism" which should be corrected to recite --is at least one of plant and a microorganism--.

In Claim 12, column 54, line 56 recites "a plant or, a microorganism" which should be corrected to recite --a plant, or a microorganism--.

In Claim 13, column 54, line 58 recites "a plant or, a microorganism" which should be corrected to recite --a plant, or a microorganism--.

In Claim 14, column 54, line 61 recites "a plant or, a microorganism" which should be corrected to recite --a plant, or a microorganism--.

Signed and Sealed this

Nineteenth Day of February, 2008

JON W. DUDAS
*Director of the United States Patent and Trademark Office*